(12) United States Patent
Huber et al.

(10) Patent No.: US 7,575,883 B2
(45) Date of Patent: Aug. 18, 2009

(54) CYTOCHROME C ACETYLATION

(75) Inventors: L. Julie Huber, Newton, MA (US); Jonathan M. Solomon, Somerville, MA (US)

(73) Assignee: Elixir Pharmaceuticals, Inc., Cambridge, MA (US)

( * ) Notice: Subject to any disclaimer, the term of this patent is extended or adjusted under 35 U.S.C. 154(b) by 93 days.

(21) Appl. No.: 10/538,823

(22) PCT Filed: Dec. 15, 2003

(86) PCT No.: PCT/US03/39794

§ 371 (c)(1), (2), (4) Date: Jun. 13, 2005

(87) PCT Pub. No.: WO2004/055169

PCT Pub. Date: Jul. 1, 2004

(65) Prior Publication Data

US 2006/0051767 A1    Mar. 9, 2006

Related U.S. Application Data

(60) Provisional application No. 60/433,096, filed on Dec. 13, 2002.

(51) Int. Cl.
| | |
|---|---|
| *C12Q 1/00* | (2006.01) |
| *G01N 33/53* | (2006.01) |
| *C12N 9/00* | (2006.01) |
| *C12N 9/99* | (2006.01) |
| *C12N 9/10* | (2006.01) |

(52) U.S. Cl. .................. 435/7.8; 435/7.71; 435/183; 435/184; 435/193; 435/18; 435/6; 435/7.1; 435/4; 435/7.6; 435/228

(58) Field of Classification Search .................. None
See application file for complete search history.

(56) References Cited

FOREIGN PATENT DOCUMENTS

WO      WO 98/58541      12/1998

OTHER PUBLICATIONS

R.A. Frye, Phylogenetic classification of prokaryotic and eukaryotic Sir2-like proteins. Biochem. Biophys. Res. Commun. 273 (2000), pp. 793-798.*
Ngo et al., in The Protein Folding Problem and Tertiary Structure Prediction, 1994, Merz et al. (ed.), Birkhauser, Boston, MA, pp. 433 and 492-495.*
Meinkoth and Wahl, Current Protocols in Molecular Biology, Hybridization Analysis of DNA Blots, pp. 2.10.8-2.10.11, 1993.*
Taft et al Trends in Genetics 22(12):649-653, 2006.*
Linder, Lab. Anim. 30(5):34-39, 2001.*
Holschneider et al, Int. J. Dev. Neuroscience 18 :615-618, 2000.*
Wood. Comp. Med. 50(1): 12-15, 2000.*
Sigmund, Arterioscler. Throm. Vasc. Biol. 20:1425-1429, 2000.*
Bilbo et al, Lab. Anim. 30(1):24-29, 2001.*
Kappel et al. Current Opinion in Biotechnology 3:558-553 1992.*
Frye, R.A., Biochemical and Biophysical Research Communications 260, 273-279 (1999).*
Cheong et al., "Induction of Apoptosis by Apicidin, a Histone Deacetylase Inhibitors Involves Reciprocal Effects on the RAF/MEK/ERK and JNK Pathways", Cancer Biology & Therapy (United States). Sep.-Oct. 2003, vol. 2, No. 5, pp. 544-551, entire document.
Marques et al., "Hemepeptide Models for Hemoproteins: the Behavior of N-acetylmicroperoxidase-11 in Aqueous Solution", Journal Inorganic Biochemistry 75:281-291, 1999, entire document.
Rieder et al., "The Cytochrome C Oxidase Binding Site on Cytochrome C: Differential Chemical Modification of Lysine Residues in Free and Oxidase-Bound Cytochrome C", Journal Biological Chemistry 253:6045-6053, Sep. 10, 1978, entire document.
Yu et al., "Induction of Apoptosis in BCR/ABL+ Cells by Histone Deacetylase Inhibitors Involves Reciprocal Effects on the RAF/MEK/ERK and JNK Pathways", Cancer Biology & Therapy (United States), 2:544-552, Sep.-Oct. 2003, entire document.

* cited by examiner

*Primary Examiner*—Rebecca E Prouty
*Assistant Examiner*—Jae W Lee
(74) *Attorney, Agent, or Firm*—Lando & Anastasi, LLP

(57) ABSTRACT

Modulation of cytochrome c acetylation, e.g., with a SIR polypeptide, enables interventions that modulate lifespan regulation and cell proliferation, e.g., by modulating apoptosis and/or mitochondrial function such as respiration.

31 Claims, 4 Drawing Sheets

SEQUENCE LISTING

<160> NUMBER OF SEQ ID NOS: 8

<210> SEQ ID NO 1
<211> LENGTH: 747
<212> TYPE: PRT
<213> ORGANISM: Homo sapiens

<400> SEQUENCE: 1

```
Met Ala Asp Glu Ala Ala Leu Ala Leu Gln Pro Gly Gly Ser Pro Ser
 1               5                  10                  15

Ala Ala Gly Ala Asp Arg Glu Ala Ala Ser Ser Pro Ala Gly Glu Pro
                20                  25                  30

Leu Arg Lys Arg Pro Arg Arg Asp Gly Pro Gly Leu Glu Arg Ser Pro
            35                  40                  45

Gly Glu Pro Gly Gly Ala Ala Pro Glu Arg Glu Val Pro Ala Ala Ala
        50                  55                  60

Arg Gly Cys Pro Gly Ala Ala Ala Ala Leu Trp Arg Glu Ala Glu
 65                  70                  75                  80

Ala Glu Ala Ala Ala Gly Gly Glu Gln Ala Gln Ala Thr Ala
                85                  90                  95

Ala Ala Gly Glu Gly Asp Asn Gly Pro Gly Leu Gln Gly Pro Ser Arg
            100                 105                 110

Glu Pro Pro Leu Ala Asp Asn Leu Tyr Asp Glu Asp Asp Asp Asp Glu
        115                 120                 125

Gly Glu Glu Glu Glu Ala Ala Ala Ala Ile Gly Tyr Arg Asp
    130                 135                 140

Asn Leu Leu Phe Gly Asp Glu Ile Ile Thr Asn Gly Phe His Ser Cys
145                 150                 155                 160

Glu Ser Asp Glu Glu Asp Arg Ala Ser His Ala Ser Ser Ser Asp Trp
                165                 170                 175

Thr Pro Arg Pro Arg Ile Gly Pro Tyr Thr Phe Val Gln Gln His Leu
            180                 185                 190

Met Ile Gly Thr Asp Pro Arg Thr Ile Leu Lys Asp Leu Leu Pro Glu
        195                 200                 205

Thr Ile Pro Pro Pro Glu Leu Asp Asp Met Thr Leu Trp Gln Ile Val
    210                 215                 220

Ile Asn Ile Leu Ser Glu Pro Pro Lys Arg Lys Lys Arg Lys Asp Ile
225                 230                 235                 240

Asn Thr Ile Glu Asp Ala Val Lys Leu Leu Gln Glu Cys Lys Lys Ile
                245                 250                 255

Ile Val Leu Thr Gly Ala Gly Val Ser Val Ser Cys Gly Ile Pro Asp
            260                 265                 270

Phe Arg Ser Arg Asp Gly Ile Tyr Ala Arg Leu Ala Val Asp Phe Pro
        275                 280                 285

Asp Leu Pro Asp Pro Gln Ala Met Phe Asp Ile Glu Tyr Phe Arg Lys
    290                 295                 300

Asp Pro Arg Pro Phe Phe Lys Phe Ala Lys Glu Ile Tyr Pro Gly Gln
305                 310                 315                 320

Phe Gln Pro Ser Leu Cys His Lys Phe Ile Ala Leu Ser Asp Lys Glu
                325                 330                 335

Gly Lys Leu Leu Arg Asn Tyr Thr Gln Asn Ile Asp Thr Leu Glu Gln
            340                 345                 350

Val Ala Gly Ile Gln Arg Ile Ile Gln Cys His Gly Ser Phe Ala Thr
```

-continued

```
                355                 360                 365
Ala Ser Cys Leu Ile Cys Lys Tyr Lys Val Asp Cys Glu Ala Val Arg
        370                 375                 380

Gly Asp Ile Phe Asn Gln Val Val Pro Arg Cys Pro Arg Cys Pro Ala
385                 390                 395                 400

Asp Glu Pro Leu Ala Ile Met Lys Pro Glu Ile Val Phe Phe Gly Glu
                405                 410                 415

Asn Leu Pro Glu Gln Phe His Arg Ala Met Lys Tyr Asp Lys Asp Glu
                420                 425                 430

Val Asp Leu Leu Ile Val Ile Gly Ser Ser Leu Lys Val Arg Pro Val
            435                 440                 445

Ala Leu Ile Pro Ser Ser Ile Pro His Glu Val Pro Gln Ile Leu Ile
        450                 455                 460

Asn Arg Glu Pro Leu Pro His Leu His Phe Asp Val Glu Leu Leu Gly
465                 470                 475                 480

Asp Cys Asp Val Ile Ile Asn Glu Leu Cys His Arg Leu Gly Gly Glu
                485                 490                 495

Tyr Ala Lys Leu Cys Cys Asn Pro Val Lys Leu Ser Glu Ile Thr Glu
            500                 505                 510

Lys Pro Pro Arg Thr Gln Lys Glu Leu Ala Tyr Leu Ser Glu Leu Pro
        515                 520                 525

Pro Thr Pro Leu His Val Ser Glu Asp Ser Ser Ser Pro Glu Arg Thr
    530                 535                 540

Ser Pro Pro Asp Ser Ser Val Ile Val Thr Leu Leu Asp Gln Ala Ala
545                 550                 555                 560

Lys Ser Asn Asp Asp Leu Asp Val Ser Glu Ser Lys Gly Cys Met Glu
                565                 570                 575

Glu Lys Pro Gln Glu Val Gln Thr Ser Arg Asn Val Glu Ser Ile Ala
            580                 585                 590

Glu Gln Met Glu Asn Pro Asp Leu Lys Asn Val Gly Ser Ser Thr Gly
        595                 600                 605

Glu Lys Asn Glu Arg Thr Ser Val Ala Gly Thr Val Arg Lys Cys Trp
    610                 615                 620

Pro Asn Arg Val Ala Lys Glu Gln Ile Ser Arg Arg Leu Asp Gly Asn
625                 630                 635                 640

Gln Tyr Leu Phe Leu Pro Pro Asn Arg Tyr Ile Phe His Gly Ala Glu
                645                 650                 655

Val Tyr Ser Asp Ser Glu Asp Val Leu Ser Ser Ser Ser Cys Gly
            660                 665                 670

Ser Asn Ser Asp Ser Gly Thr Cys Gln Ser Pro Ser Leu Glu Glu Pro
        675                 680                 685

Met Glu Asp Glu Ser Glu Ile Glu Glu Phe Tyr Asn Gly Leu Glu Asp
    690                 695                 700

Glu Pro Asp Val Pro Glu Arg Ala Gly Gly Ala Gly Phe Gly Thr Asp
705                 710                 715                 720

Gly Asp Asp Gln Glu Ala Ile Asn Glu Ala Ile Ser Val Lys Gln Glu
                725                 730                 735

Val Thr Asp Met Asn Tyr Pro Ser Asn Lys Ser
            740                 745

<210> SEQ ID NO 2
<211> LENGTH: 389
<212> TYPE: PRT
<213> ORGANISM: Homo sapiens
```

<400> SEQUENCE: 2

```
Met Ala Glu Pro Asp Pro Ser His Pro Leu Glu Thr Gln Ala Gly Lys
1               5                   10                  15
Val Gln Glu Ala Gln Asp Ser Asp Ser Asp Ser Glu Gly Gly Ala Ala
            20                  25                  30
Gly Gly Glu Ala Asp Met Asp Phe Leu Arg Asn Leu Phe Ser Gln Thr
        35                  40                  45
Leu Ser Leu Gly Ser Gln Lys Glu Arg Leu Leu Asp Glu Leu Thr Leu
    50                  55                  60
Glu Gly Val Ala Arg Tyr Met Gln Ser Glu Arg Cys Arg Arg Val Ile
65                  70                  75                  80
Cys Leu Val Gly Ala Gly Ile Ser Thr Ser Ala Gly Ile Pro Asp Phe
                85                  90                  95
Arg Ser Pro Ser Thr Gly Leu Tyr Asp Asn Leu Glu Lys Tyr His Leu
            100                 105                 110
Pro Tyr Pro Glu Ala Ile Phe Glu Ile Ser Tyr Phe Lys Lys His Pro
        115                 120                 125
Glu Pro Phe Phe Ala Leu Ala Lys Glu Leu Tyr Pro Gly Gln Phe Lys
    130                 135                 140
Pro Thr Ile Cys His Tyr Phe Met Arg Leu Leu Lys Asp Lys Gly Leu
145                 150                 155                 160
Leu Leu Arg Cys Tyr Thr Gln Asn Ile Asp Thr Leu Glu Arg Ile Ala
                165                 170                 175
Gly Leu Glu Gln Glu Asp Leu Val Glu Ala His Gly Thr Phe Tyr Thr
            180                 185                 190
Ser His Cys Val Ser Ala Ser Cys Arg His Glu Tyr Pro Leu Ser Trp
        195                 200                 205
Met Lys Glu Lys Ile Phe Ser Glu Val Thr Pro Lys Cys Glu Asp Cys
    210                 215                 220
Gln Ser Leu Val Lys Pro Asp Ile Val Phe Phe Gly Glu Ser Leu Pro
225                 230                 235                 240
Ala Arg Phe Phe Ser Cys Met Gln Ser Asp Phe Leu Lys Val Asp Leu
                245                 250                 255
Leu Leu Val Met Gly Thr Ser Leu Gln Val Gln Pro Phe Ala Ser Leu
            260                 265                 270
Ile Ser Lys Ala Pro Leu Ser Thr Pro Arg Leu Leu Ile Asn Lys Glu
        275                 280                 285
Lys Ala Gly Gln Ser Asp Pro Phe Leu Gly Met Ile Met Gly Leu Gly
    290                 295                 300
Gly Gly Met Asp Phe Asp Ser Lys Lys Ala Tyr Arg Asp Val Ala Trp
305                 310                 315                 320
Leu Gly Glu Cys Asp Gln Gly Cys Leu Ala Leu Ala Glu Leu Leu Gly
                325                 330                 335
Trp Lys Lys Glu Leu Glu Asp Leu Val Arg Arg Glu His Ala Ser Ile
            340                 345                 350
Asp Ala Gln Ser Gly Ala Gly Val Pro Asn Pro Ser Thr Ser Ala Ser
        355                 360                 365
Pro Lys Lys Ser Pro Pro Ala Lys Asp Glu Ala Arg Thr Thr Glu
    370                 375                 380
Arg Glu Lys Pro Gln
385
```

<210> SEQ ID NO 3
<211> LENGTH: 399
<212> TYPE: PRT
<213> ORGANISM: Homo sapiens

<400> SEQUENCE: 3

Met Ala Phe Trp Gly Trp Arg Ala Ala Ala Leu Arg Leu Trp Gly
 1               5                  10                  15

Arg Val Val Glu Arg Val Glu Ala Gly Gly Val Gly Pro Phe Gln
            20                  25                  30

Ala Cys Gly Cys Arg Leu Val Leu Gly Gly Arg Asp Asp Val Ser Ala
         35                  40                  45

Gly Leu Arg Gly Ser His Gly Ala Arg Gly Glu Pro Leu Asp Pro Ala
     50                  55                  60

Arg Pro Leu Gln Arg Pro Pro Arg Pro Glu Val Pro Arg Ala Phe Arg
 65                  70                  75                  80

Arg Gln Pro Arg Ala Ala Ala Pro Ser Phe Phe Phe Ser Ser Ile Lys
                 85                  90                  95

Gly Gly Arg Arg Ser Ile Ser Phe Ser Val Gly Ala Ser Ser Val Val
            100                 105                 110

Gly Ser Gly Gly Ser Ser Asp Lys Gly Lys Leu Ser Leu Gln Asp Val
        115                 120                 125

Ala Glu Leu Ile Arg Ala Arg Ala Cys Gln Arg Val Val Val Met Val
    130                 135                 140

Gly Ala Gly Ile Ser Thr Pro Ser Gly Ile Pro Asp Phe Arg Ser Pro
145                 150                 155                 160

Gly Ser Gly Leu Tyr Ser Asn Leu Gln Gln Tyr Asp Leu Pro Tyr Pro
                165                 170                 175

Glu Ala Ile Phe Glu Leu Pro Phe Phe Phe His Asn Pro Lys Pro Phe
            180                 185                 190

Phe Thr Leu Ala Lys Glu Leu Tyr Pro Gly Asn Tyr Lys Pro Asn Val
        195                 200                 205

Thr His Tyr Phe Leu Arg Leu Leu His Asp Lys Gly Leu Leu Leu Arg
    210                 215                 220

Leu Tyr Thr Gln Asn Ile Asp Gly Leu Glu Arg Val Ser Gly Ile Pro
225                 230                 235                 240

Ala Ser Lys Leu Val Glu Ala His Gly Thr Phe Ala Ser Ala Thr Cys
                245                 250                 255

Thr Val Cys Gln Arg Pro Phe Pro Gly Glu Asp Ile Arg Ala Asp Val
            260                 265                 270

Met Ala Asp Arg Val Pro Arg Cys Pro Val Cys Thr Gly Val Val Lys
        275                 280                 285

Pro Asp Ile Val Phe Phe Gly Glu Pro Leu Pro Gln Arg Phe Leu Leu
    290                 295                 300

His Val Asp Phe Pro Met Ala Asp Leu Leu Leu Ile Leu Gly Thr
305                 310                 315                 320

Ser Leu Glu Val Glu Pro Phe Ala Ser Leu Thr Glu Ala Val Arg Ser
                325                 330                 335

Ser Val Pro Arg Leu Leu Ile Asn Arg Asp Leu Val Gly Pro Leu Ala
            340                 345                 350

Trp His Pro Arg Ser Arg Asp Val Ala Gln Leu Gly Asp Val Val His
        355                 360                 365

Gly Val Glu Ser Leu Val Glu Leu Leu Gly Trp Thr Glu Glu Met Arg
    370                 375                 380

Asp Leu Val Gln Arg Glu Thr Gly Lys Leu Asp Gly Pro Asp Lys
385                 390                 395

<210> SEQ ID NO 4
<211> LENGTH: 314
<212> TYPE: PRT
<213> ORGANISM: Homo sapiens

<400> SEQUENCE: 4

Met Lys Met Ser Phe Ala Leu Thr Phe Arg Ser Ala Lys Gly Arg Trp
1               5                   10                  15

Ile Ala Asn Pro Ser Gln Pro Cys Ser Lys Ala Ser Ile Gly Leu Phe
            20                  25                  30

Val Pro Ala Ser Pro Pro Leu Asp Pro Glu Lys Val Lys Glu Leu Gln
        35                  40                  45

Arg Phe Ile Thr Leu Ser Lys Arg Leu Leu Val Met Thr Gly Ala Gly
    50                  55                  60

Ile Ser Thr Glu Ser Gly Ile Pro Asp Tyr Arg Ser Glu Lys Val Gly
65                  70                  75                  80

Leu Tyr Ala Arg Thr Asp Arg Arg Pro Ile Gln His Gly Asp Phe Val
                85                  90                  95

Arg Ser Ala Pro Ile Arg Gln Arg Tyr Trp Ala Arg Asn Phe Val Gly
            100                 105                 110

Trp Pro Gln Phe Ser Ser His Gln Pro Asn Pro Ala His Trp Ala Leu
        115                 120                 125

Ser Thr Trp Glu Lys Leu Gly Lys Leu Tyr Trp Leu Val Thr Gln Asn
    130                 135                 140

Val Asp Ala Leu His Thr Lys Ala Gly Ser Arg Arg Leu Thr Glu Leu
145                 150                 155                 160

His Gly Cys Met Asp Arg Val Leu Cys Leu Asp Cys Gly Glu Gln Thr
                165                 170                 175

Pro Arg Gly Val Leu Gln Glu Arg Phe Gln Val Leu Asn Pro Thr Trp
            180                 185                 190

Ser Ala Glu Ala His Gly Leu Ala Pro Asp Gly Asp Val Phe Leu Ser
        195                 200                 205

Glu Glu Gln Val Arg Ser Phe Gln Val Pro Thr Cys Val Gln Cys Gly
    210                 215                 220

Gly His Leu Lys Pro Asp Val Val Phe Phe Gly Asp Thr Val Asn Pro
225                 230                 235                 240

Asp Lys Val Asp Phe Val His Lys Arg Val Lys Glu Ala Asp Ser Leu
                245                 250                 255

Leu Val Val Gly Ser Ser Leu Gln Val Tyr Ser Gly Tyr Arg Phe Ile
            260                 265                 270

Leu Thr Ala Trp Glu Lys Lys Leu Pro Ile Ala Ile Leu Asn Ile Gly
        275                 280                 285

Pro Thr Arg Ser Asp Asp Leu Ala Cys Leu Lys Leu Asn Ser Arg Cys
    290                 295                 300

Gly Glu Leu Leu Pro Leu Ile Asp Pro Cys
305                 310

<210> SEQ ID NO 5
<211> LENGTH: 310
<212> TYPE: PRT
<213> ORGANISM: Homo sapiens

<400> SEQUENCE: 5

Met Arg Pro Leu Gln Ile Val Pro Ser Arg Leu Ile Ser Gln Leu Tyr
1               5                   10                  15

Cys Gly Leu Lys Pro Pro Ala Ser Thr Arg Asn Gln Ile Cys Leu Lys
                20                  25                  30

Met Ala Arg Pro Ser Ser Met Ala Asp Phe Arg Lys Phe Phe Ala
        35                  40                  45

Lys Ala Lys His Ile Val Ile Ile Ser Gly Ala Gly Val Ser Ala Glu
50                  55                  60

Ser Gly Val Pro Thr Phe Arg Gly Ala Gly Gly Tyr Trp Arg Lys Trp
65                  70                  75                  80

Gln Ala Gln Asp Leu Ala Thr Pro Leu Ala Phe Ala His Asn Pro Ser
                85                  90                  95

Arg Val Trp Glu Phe Tyr His Tyr Arg Arg Glu Val Met Gly Ser Lys
                100                 105                 110

Glu Pro Asn Ala Gly His Arg Ala Ile Ala Glu Cys Glu Thr Arg Leu
            115                 120                 125

Gly Lys Gln Gly Arg Arg Val Val Val Ile Thr Gln Asn Ile Asp Glu
        130                 135                 140

Leu His Arg Lys Ala Gly Thr Lys Asn Leu Leu Glu Ile His Gly Ser
145                 150                 155                 160

Leu Phe Lys Thr Arg Cys Thr Ser Cys Gly Val Val Ala Glu Asn Tyr
                165                 170                 175

Lys Ser Pro Ile Cys Pro Ala Leu Ser Gly Lys Gly Ala Pro Glu Pro
                180                 185                 190

Gly Thr Gln Asp Ala Ser Ile Pro Val Glu Lys Leu Pro Arg Cys Glu
            195                 200                 205

Glu Ala Gly Cys Gly Gly Leu Leu Arg Pro His Val Val Trp Phe Gly
210                 215                 220

Glu Asn Leu Asp Pro Ala Ile Leu Glu Glu Val Asp Arg Glu Leu Ala
225                 230                 235                 240

His Cys Asp Leu Cys Leu Val Val Gly Thr Ser Ser Val Val Tyr Pro
                245                 250                 255

Ala Ala Met Phe Ala Pro Gln Val Ala Ala Arg Gly Val Pro Val Ala
                260                 265                 270

Glu Phe Asn Thr Glu Thr Thr Pro Ala Thr Asn Arg Phe Arg Phe His
                275                 280                 285

Phe Gln Gly Pro Cys Gly Thr Thr Leu Pro Glu Ala Leu Ala Cys His
            290                 295                 300

Glu Asn Glu Thr Val Ser
305                 310

<210> SEQ ID NO 6
<211> LENGTH: 355
<212> TYPE: PRT
<213> ORGANISM: Homo sapiens

<400> SEQUENCE: 6

Met Ser Val Asn Tyr Ala Ala Gly Leu Ser Pro Tyr Ala Asp Lys Gly
1               5                   10                  15

Lys Cys Gly Leu Pro Glu Ile Phe Asp Pro Pro Glu Glu Leu Glu Arg
                20                  25                  30

Lys Val Trp Glu Leu Ala Arg Leu Val Trp Gln Ser Ser Ser Val Val
            35                  40                  45

Phe His Thr Gly Ala Gly Ile Ser Thr Ala Ser Gly Ile Pro Asp Phe
50                  55                  60

```
Arg Gly Pro His Gly Val Trp Thr Met Glu Glu Arg Gly Leu Ala Pro
 65                  70                  75                  80

Lys Phe Asp Thr Thr Phe Glu Ser Ala Arg Pro Thr Gln Thr His Met
                 85                  90                  95

Ala Leu Val Gln Leu Glu Arg Val Gly Leu Leu Arg Phe Leu Val Ser
            100                 105                 110

Gln Asn Val Asp Gly Leu His Val Arg Ser Gly Phe Pro Arg Asp Lys
            115                 120                 125

Leu Ala Glu Leu His Gly Asn Met Phe Val Glu Glu Cys Ala Lys Cys
        130                 135                 140

Lys Thr Gln Tyr Val Arg Asp Thr Val Val Gly Thr Met Gly Leu Lys
145                 150                 155                 160

Ala Thr Gly Arg Leu Cys Thr Val Ala Lys Ala Arg Gly Leu Arg Ala
                165                 170                 175

Cys Arg Gly Glu Leu Arg Asp Thr Ile Leu Asp Trp Glu Asp Ser Leu
            180                 185                 190

Pro Asp Arg Asp Leu Ala Leu Ala Asp Glu Ala Ser Arg Asn Ala Asp
        195                 200                 205

Leu Ser Ile Thr Leu Gly Thr Ser Leu Gln Ile Arg Pro Ser Gly Asn
210                 215                 220

Leu Pro Leu Ala Thr Lys Arg Gly Gly Arg Leu Val Ile Val Asn
225                 230                 235                 240

Leu Gln Pro Thr Lys His Asp Arg His Ala Asp Leu Arg Ile His Gly
                245                 250                 255

Tyr Val Asp Glu Val Met Thr Arg Leu Met Lys His Leu Gly Leu Glu
            260                 265                 270

Ile Pro Ala Trp Asp Gly Pro Arg Val Leu Glu Arg Ala Leu Pro Pro
        275                 280                 285

Leu Pro Arg Pro Pro Thr Pro Lys Leu Glu Pro Lys Glu Glu Ser Pro
290                 295                 300

Thr Arg Ile Asn Gly Ser Ile Pro Ala Gly Pro Lys Gln Glu Pro Cys
305                 310                 315                 320

Ala Gln His Asn Gly Ser Glu Pro Ala Ser Pro Lys Arg Glu Arg Pro
                325                 330                 335

Thr Ser Pro Ala Pro His Arg Pro Pro Lys Arg Val Lys Ala Lys Ala
            340                 345                 350

Val Pro Ser
        355

<210> SEQ ID NO 7
<211> LENGTH: 400
<212> TYPE: PRT
<213> ORGANISM: Homo sapiens

<400> SEQUENCE: 7

Met Ala Ala Gly Gly Leu Ser Arg Ser Glu Arg Lys Ala Ala Glu Arg
 1               5                  10                  15

Val Arg Arg Leu Arg Glu Glu Gln Arg Glu Arg Leu Arg Gln Val
             20                  25                  30

Ser Arg Ile Leu Arg Lys Ala Ala Ala Glu Arg Ser Ala Glu Glu Gly
             35                  40                  45

Arg Leu Leu Ala Glu Ser Ala Asp Leu Val Thr Glu Leu Gln Gly Arg
         50                  55                  60

Ser Arg Arg Arg Glu Gly Leu Lys Arg Arg Gln Glu Glu Val Cys Asp
```

```
                65                  70                  75                  80
Asp Pro Glu Glu Leu Arg Gly Lys Val Arg Glu Leu Ala Ser Ala Val
                    85                  90                  95
Arg Asn Ala Lys Tyr Leu Val Val Tyr Thr Gly Ala Gly Ile Ser Thr
                100                 105                 110
Ala Ala Ser Ile Pro Asp Tyr Arg Gly Pro Asn Gly Val Trp Thr Leu
                115                 120                 125
Leu Gln Lys Gly Arg Ser Val Ser Ala Ala Asp Leu Ser Glu Ala Glu
        130                 135                 140
Pro Thr Leu Thr His Met Ser Ile Thr Arg Leu His Glu Gln Lys Leu
145                 150                 155                 160
Val Gln His Val Val Ser Gln Asn Cys Asp Gly Leu His Leu Arg Ser
                165                 170                 175
Gly Leu Pro Arg Thr Ala Ile Ser Glu Leu His Gly Asn Met Tyr Ile
                180                 185                 190
Glu Val Cys Thr Ser Cys Val Pro Asn Arg Glu Tyr Val Arg Val Phe
                195                 200                 205
Asp Val Thr Glu Arg Thr Ala Leu His Arg His Gln Thr Gly Arg Thr
        210                 215                 220
Cys His Lys Cys Gly Thr Gln Leu Arg Asp Thr Ile Val His Phe Gly
225                 230                 235                 240
Glu Arg Gly Thr Leu Gly Gln Pro Leu Asn Trp Glu Ala Ala Thr Glu
                245                 250                 255
Ala Ala Ser Arg Ala Asp Thr Ile Leu Cys Leu Gly Ser Ser Leu Lys
                260                 265                 270
Val Leu Lys Lys Tyr Pro Arg Leu Trp Cys Met Thr Lys Pro Pro Ser
            275                 280                 285
Arg Arg Pro Lys Leu Tyr Ile Val Asn Leu Gln Trp Thr Pro Lys Asp
        290                 295                 300
Asp Trp Ala Ala Leu Lys Leu His Gly Lys Cys Asp Asp Val Met Arg
305                 310                 315                 320
Leu Leu Met Ala Glu Leu Gly Leu Glu Ile Pro Ala Tyr Ser Arg Trp
                325                 330                 335
Gln Asp Pro Ile Phe Ser Leu Ala Thr Pro Leu Arg Ala Gly Glu Glu
                340                 345                 350
Gly Ser His Ser Arg Lys Ser Leu Cys Arg Ser Arg Glu Glu Ala Pro
            355                 360                 365
Pro Gly Asp Arg Gly Ala Pro Leu Ser Ser Ala Pro Ile Leu Gly Gly
        370                 375                 380
Trp Phe Gly Arg Gly Cys Thr Lys Arg Thr Lys Arg Lys Lys Val Thr
385                 390                 395                 400

<210> SEQ ID NO 8
<211> LENGTH: 104
<212> TYPE: PRT
<213> ORGANISM: Homo sapiens

<400> SEQUENCE: 8

Gly Asp Val Glu Lys Gly Lys Lys Ile Phe Ile Met Lys Cys Ser Gln
1               5                   10                  15
Cys His Thr Val Glu Lys Gly Gly Lys His Lys Thr Gly Pro Asn Leu
                20                  25                  30
His Gly Leu Phe Gly Arg Lys Thr Gly Gln Ala Pro Gly Tyr Ser Tyr
            35                  40                  45
```

```
-continued

Thr Ala Ala Asn Lys Asn Lys Gly Ile Ile Trp Gly Glu Asp Thr Leu
    50              55                  60

Met Glu Tyr Leu Glu Asn Pro Lys Lys Tyr Ile Pro Gly Thr Lys Met
65              70                  75                  80

Ile Phe Val Gly Ile Lys Lys Lys Glu Glu Arg Ala Asp Leu Ile Ala
                85              90                      95

Tyr Leu Lys Lys Ala Thr Asn Glu
            100
```

US 7,575,883 B2

CYTOCHROME C ACETYLATION

CROSS-REFERENCE TO RELATED APPLICATIONS

This application claims priority to U.S. Application Ser. No. 60/433,096, filed on Dec. 13, 2002, the contents of which are incorporated by reference herein for all purposes.

BACKGROUND OF THE INVENTION

Cytochrome c has been identified as an important participant in apoptosis. In living cells, cytochrome c is present in the intermembrane space of the mitochondria, where it plays a role in respiration. During apoptosis, however, cytochrome c translocates to the cytosol. Green et al. (1998) Cell 94:695-698; Martinou et al. (1999) Nature 399:411-412. Mitochondrial-produced reactive oxygen species (ROS) occur in bursts in the mitochondria and are involved in release of cytochrome c into the cytosol. Kirkland (2001) J. Neurosci 21(6):1949-1963. In the cytosol, cytochrome c binds to Apaf-1 in a dATP/ATP dependent manner, precipitating the oligomerization of Apaf-1. Kluck et al. (2000) J. Biol. Chem. 21:16127-16133. The ensuing recruitment and activation of caspase-9 results in the activation of further caspases, including caspase-3. These caspases in turn cleave many important substrates and orchestrate the final packaging of the apoptotic cell. Liu et al. (1997) Cell 89:175-184; Enari et al. (1998) Nature 391:43-50; Sahara (199) Nature 401:168-173.

SUMMARY OF THE INVENTION

The invention is based, in part, on the discovery that by modulating acetylation of cytochrome c, cytochrome c induced cellular processes such as apoptosis and mitochondrial function (e.g., respiration) can be modulated. For example, it has been found that proteins of the Silent Information Regulator (SIR) family, such as SIRT1, SIRT2, SIRT3, SIRT4, SIRT5, SIRT6 and SIRT7, interact with cytochrome c and reduce acetylation of cytochrome c, thereby affecting apoptosis and/or mitochondrial function. Accordingly, the invention relates to methods and compositions employing a polypeptide (or polypeptides) having the ability to modulate acetylation (e.g., a SIR polypeptide or polypeptides) and agonists or antagonists thereof to modulate cytochrome c related processes such as apoptosis or mitochondrial function.

In one aspect, the invention features a method of screening a compound, e.g., for its effect on the acetylation status of a cytochrome c polypeptide. The method includes providing a compound, e.g., a compound which interacts with (e.g., binds to) cytochrome c; contacting a cytochrome c polypeptide with the compound and evaluating a chemical reaction, e.g., the effect of the compound on the acetylation of the cytochrome c polypeptide.

In a preferred embodiment, the cytochrome c polypeptide is acetylated and the ability of the compound to deacetylate the cytochrome c polypeptide is evaluated. The acetylated cytochrome c polypeptide can include a moiety that can be spectroscopically detected, e.g., a fluorophore or a chromophore. Cytochrome c can also be evaluated, e.g., using mass spectroscopy (e.g., MALDI-TOF), or an immunoassay, e.g., using an antibody (e.g., an antibody specific for an acetylated form) or other specific binding agent.

The method can include, e.g., evaluating the cytochrome c polypeptide directly, evaluating a modification product of the cytochrome c polypeptide (e.g., by contacting a reaction component to a developer, e.g., a protease), or evaluating a reaction substrate (e.g., the cytochrome c polypeptide or NAD) or byproduct (e.g., nicotinamide or O-acetyl ADP ribose) or parameter (e.g., temperature, pH).

The cytochrome c polypeptide can be a full length cytochrome c or a fragment thereof, e.g., a peptide of at least 3, 4, 5, or more amino acids, e.g., between 3-12 or 4-10 amino acids. The cytochrome c polypeptide can be from a mammalian cytochrome c, e.g., a human, rat, mouse, canine, ovine, or bovine cytochrome c.

In one embodiment, the compound is other than a SIR protein, or other than a protein.

In one embodiment, the method includes providing a SIR protein in addition to the compound.

In one embodiment, the compound is a SIR protein, e.g., a wildtype or mutant SIR protein In some embodiments, the interaction between the compound and cytochrome c polypeptide is evaluated in vitro, e.g., using an isolated polypeptide. The cytochrome c polypeptide can be in solution (e.g., in a micelle) or bound to a solid support, e.g., a column, agarose beads, a plastic well or dish, or a chip (e.g., a microarray). Similarly, the compound can be in solution or bound to a solid support.

In other embodiments, interaction of a compound with the cytochrome c polypeptide and/or the ability of the compound to effect the acetylation status of the cytochrome c polypeptide can be evaluated using a cell-based assay. For example, the cell can be a yeast cell, an invertebrate cell (e.g., a fly cell), or a vertebrate cell (e.g., a Xenopus oocyte or a mammalian cell, e.g., a mouse or human cell).

In preferred embodiments, the cell-based assay measures the acetylation or deacetylation of the cytochrome c polypeptide and/or measures the binding of cytochrome c to a second protein (e.g., Apaf-1 or a fragment thereof) and/or measures cell viability and apoptosis, to evaluate the acetylation status of cytochrome c. In other embodiments, a compound identified as altering the acetylation status of cytochrome c can be evaluated for its effect on mitochondrial function such as respiration.

Possible test compounds include, e.g., small organic and inorganic molecules, peptides, antibodies, and nucleic acid molecules.

In one embodiment, a co-factor for deacetylation activity, e.g., a SIR polypeptide co-factor, such as NAD or an NAD analog, is also present.

In some embodiments, one or more steps of the method are repeated one or more times such that, e.g., a library of test compounds can be evaluated.

In another aspect, the invention features a method of screening a compound, e.g., a compound which modulates, e.g., increases or decreases, interaction between a polypeptide which modulates acetylation, e.g., a polypeptide having deacetylation activity, and cytochrome c. The method includes: contacting a polypeptide having acetylation or deacetylation activity or fragment thereof, with a compound, e.g., a modulator of the polypeptide, in the presence of cytochrome c or a fragment thereof, and determining if the compound modulates interaction, e.g., binding, between the polypeptide and the cytochrome c. In one embodiment, the polypeptide has deacetylation activity and is, e.g., a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof. In some embodiments, the ability of the compound to modulate interaction, e.g., binding, between the polypeptide and cytochrome c can be determined by evaluating the interaction, e.g., binding, of the polypeptide or fragment thereof, and the cytochrome c or fragment thereof in the absence of the compound. Possible compounds include, e.g., small organic or inorganic molecules, peptides, antibodies, and nucleic acid molecules.

In one embodiment, a co-factor for deacetylation activity, e.g., a SIR polypeptide co-factor, such as NAD or an NAD analog, is also present during the contacting step.

In one embodiment, the cytochrome c or a fragment thereof, is acetylated or labeled.

In some embodiments, the method further includes determining if the compound modulates acetylation of cytochrome c. For example, acetylation of the cytochrome c or fragment thereof can be evaluated in the absence and presence of the compound to determine the effect the compound has on the polypeptide acetylation or deacetylation activity.

In some embodiments, the method is repeated one or more times such that, e.g., a library of test compounds can be evaluated.

In some embodiments, the method can further include evaluating a compound that modulates interaction between a polypeptide having acetylation or deacetylation activity, or a fragment thereof, and cytochrome c, or fragment thereof, to determine its effect on a parameter of a cell, for example, an age-associated parameter of a cell (e.g., a fibroblast, an osteoblast, a skin cell, a blood cell, a transformed cell, a senescent cell, a cultured cell or a neural cell), e.g., by contacting the cell with the compound. In such embodiments, modulation of the interaction of the polypeptide and a cytochrome c and modulation of an age-associated parameter relative to a control cell identifies the compound as having a modulatory effect on life span regulation. Such compounds can, e.g., be identified as a candidate for modulating, e.g., slowing or speeding, age, modulating, e.g., increasing or decreasing lifespan, modulating, e.g., increasing or decreasing metabolism (e.g., by increasing or decreasing metabolic function and/or rate), modulating, e.g., increasing or decreasing electron transport. The age associated parameter can be, e.g., one or more of: (i) lifespan of the cell; (ii) presence or abundance of a gene transcript or gene product in a cell or organism that has a biological age dependent expression pattern; (iii) resistance of the cell or organism to stress; (iv) one or more metabolic parameters of the cell or organism; (v) proliferative capacity of the cell or a set of cells present in the organism. In some embodiments, the parameter is one or more of (i) the proliferative capacity of the cell or a set of cells in an organism and (ii) apoptosis of the cell or a set of cells in the organism, and, e.g., compounds which decrease the proliferative capacity can be identified as candidate compounds for treating or preventing a disorder associated with unwanted cell proliferation, e.g., cancer.

In another aspect, the invention features a method of screening a compound, e.g., a compound which modulates acetylation or deacetylation activity of a polypeptide. The method includes: contacting a cell which expresses a polypeptide having acetylation or deacetylation activity and cytochrome c (or fragments thereof) with a compound, and determining if the compound modulates, e.g., increases or decreases, acetylation of cytochrome c. In one embodiment, the polypeptide has deacetylation activity and is, e.g., a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof. Compounds which increase acetylation of cytochrome c can be identified as compounds which inhibit or reduce a SIR polypeptide activity, i.e., deacetylation. Compounds which modulate acetylation of cytochrome c can be identified as compounds which modulate acetylation or deacetylation activity of the polypeptide. Possible compounds include, e.g., small organic or inorganic molecules, peptides, antibodies, and nucleic acid molecules.

In some embodiments, the ability of a compound to modulate acetylation can be evaluated by determining increases or decreases in the interaction, e.g., binding, of cytochrome c and a secondary protein (e.g., an Apaf-1 protein or fragment thereof). The ability of a compound to modulate the acetylation or deacetylation activity of the polypeptide, e.g., increase or decrease polypeptide deacetylation activity, can be accomplished by comparing the interaction, e.g., binding, of cytochrome c and Apaf-1 in the cell in the absence and presence of the compound. Compounds which increase the interaction between cytochrome c and Apaf-1 can be identified as compounds which decrease acetylation and/or increase deacetylation of cytochrome c. Compounds which decrease the interaction can be identified as compounds which increase acetylation and/or decrease deacetylation of cytochrome c. In other embodiments, the ability of a compound to modulate acetylation can be identified by evaluating acetylation, e.g., in the absence and presence of the compound.

In one embodiment, a co-factor for deacetylation activity, e.g., a SIR polypeptide co-factor, such as NAD or a NAD analog, is also present.

In one embodiment, the cytochrome c or a fragment thereof, is acetylated or labeled.

In some embodiments, the method is repeated one or more times such that, e.g., a library of test compounds can be evaluated.

In some embodiments, the method can further include evaluating a compound that modulates the acetylation or deacetylation activity of the polypeptide, to determine its effect on a parameter of a cell, for example, an age-associated parameter of a cell (e.g., a fibroblast, an osteoblast, a skin cell, a blood cell, a transformed cell, a senescent cell, a cultured cell or a neural cell). The cell can be the same cell used to evaluate the ability of the compound to modulate the polypeptide's acetylation or deacetylation capacity, or it can be a different cell which is contacted with the compound. In such embodiments, modulation of the polypeptide's acetylation or deacetylation capacity and modulation of an age-associated parameter relative to a control cell identify the compound as having a modulatory effect on life span regulation. Such compounds can be identified as candidates for modulating, e.g., slowing or speeding, age, modulating, e.g., increasing or decreasing lifespan, modulating, e.g., increasing or decreasing metabolism (e.g., by increasing or decreasing metabolic function and/or rate), modulating, e.g., increasing or decreasing, electron transport. The age-associated parameter can be, e.g., one or more of: (i) lifespan of the cell; (ii) presence or abundance of a gene transcript or gene product in a cell or organism that has a biological age dependent expression pattern; (iii) resistance of the cell or organism to stress; (iv) one or more metabolic parameters of the cell or organism; (v) proliferative capacity of the cell or a set of cells present in the organism. In some embodiments, the parameter is one or more of (i) the proliferative capacity of the cell or a set of cells in an organism and (ii) apoptosis of the cell or a set of cells in the organism, and, e.g., compounds which decrease the proliferative capacity can be identified as candidate compounds for treating or preventing a disorder associated with unwanted cell proliferation, e.g., cancer.

In another aspect, the invention features a method of screening a compound which includes: providing a compound which interacts with cytochrome c or a polypeptide having acetylation or deacetylation activity, e.g., a compound that binds the polypeptide or cytochrome c; contacting a cell or organism that expresses the polypeptide or cytochrome c with the compound, and evaluating the effect of the compound on acetylation or deacetylation of cytochrome c. In one embodiment, the polypeptide has deacetylation activity and is, e.g., a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof.

In other embodiments, the method further includes evaluating a cell or organism to determine the effect of the compound on a parameter of a cell, for example, an age-associated parameter of a cell (e.g., a fibroblast, an osteoblast, a skin cell, a blood cell, a transformed cell, a senescent cell, a cultured cell or a neural cell). The cell can be the same cell used to evaluate the ability of the compound to modulate the polypeptide's acetylation or deacetylation capacity, or it can be a different cell which is contacted with the compound. In such embodiments, interaction with the polypeptide or cytochrome c and modulation of an age-associated parameter relative to a control cell identifies the compound as having a modulatory effect on life span regulation. Such compounds can be identified as candidates for modulating, e.g., slowing or speeding, age, modulating, e.g., increasing or decreasing lifespan, modulating, e.g., increasing or decreasing metabolism (e.g., by increasing or decreasing metabolic function and/or rate), modulating, e.g., increasing or decreasing electron transport. The age-associated parameter can be, e.g., one or more of: (i) lifespan of the cell; (ii) presence or abundance of a gene transcript or gene product in a cell or organism that has a biological age dependent expression pattern; (iii) resistance of the cell or organism to stress, e.g., genotoxic stress (e.g., etopicide, UV irradiation, exposure to a mutagen, and so forth) or oxidative stress or hypoxic stress; (iv) one or more metabolic parameters of the cell or organism (e.g., protein synthesis or degradation, ubiquinone biosynthesis, cholesterol biosynthesis, ATP levels, glucose metabolism, nucleic acid metabolism, ribosomal translation rates, etc.); (v) proliferative capacity of the cell or a set of cells present in the organism (e.g., of retinal cells, bone cells, white blood cells, etc.). Alternatively, evaluating the rate of aging can include directly measuring the average life span of a group of animals (e.g., a group of genetically matched animals) and comparing the resulting average to the average life span of a control group of animals (e.g., a group of animals that did not receive the compound but are genetically matched to the group of animals that did receive the test compound). In other embodiments, the parameter is one or more of (i) the proliferative capacity of the cell or a set of cells in an organism and (ii) apoptosis of the cell or a set of cells in the organism, and, e.g., compounds which decrease the proliferative capacity can be identified as candidate compounds for treating or preventing a disorder associated with unwanted cell proliferation, e.g., cancer.

In some embodiments, the cell is a transgenic cell, e.g., a cell having a transgene. In some embodiments, the transgene encodes a protein that is normally exogenous to the transgenic cell. In some embodiments, the transgene encodes a human protein, e.g., a human polypeptide having acetylation or deacetylation activity (e.g., a SIR polypeptide) or a human cytochrome c polypeptide. In some embodiments, the transgene is linked to a heterologous promoter. In other embodiments, the transgene is linked to its native promoter. In some embodiments, the cell is isolated from an organism that has been contacted with the compound. In other embodiments, the cell is contacted directly with the compound.

In some embodiments, the organism is on a calorically rich diet, while in other embodiments the organism is on a calorically restricted diet.

In some embodiments, a portion of the organism's life, e.g., at least 20%, 30%, 40%, 50%, 60%, 70%, 80%, 90%, or more, of the expected life span of the organism, has elapsed prior to the organism being contacted with the compound.

In some embodiments, the method can further include evaluating the ability of the compound to interact, e.g., bind to a polypeptide having acetylation or deacetylation activity or a cytochrome c polypeptide, e.g., evaluating the interaction prior to evaluating the effect of the compound on a cell or organism. In some embodiments, the interaction between the test compound and the polypeptide or cytochrome c is evaluated in vitro, e.g., using an isolated polypeptide. The polypeptide or cytochrome c polypeptide can be in solution (e.g., in a micelle) or bound to a solid support, e.g., a column, agarose beads, a plastic well or dish, or a chip (e.g., a microarray). Similarly, the test compound can be in solution or bound to a solid support.

In other embodiments, when the method includes evaluating the ability of the compound to interact, e.g., bind to, the polypeptide or cytochrome c, the interaction between the compound and the polypeptide or cytochrome c is evaluated using a cell-based assay. For example, the cell can be a yeast cell, an invertebrate cell (e.g., a fly cell), or a vertebrate cell (e.g., a *Xenopus* oocyte or a mammalian cell, e.g., a mouse or human cell). In preferred embodiments, the cell-based assay measures the activity or expression levels of the polypeptide or cytochrome c.

Possible test compounds include, e.g., small organic or inorganic molecules, peptides, antibodies, and nucleic acid molecules.

In one embodiment, a co-factor for deacetylation activity, e.g., a SIR polypeptide co-factor, such as NAD or an NAD analog, is also present.

In one embodiment, the cytochrome c or a fragment thereof, is acetylated or labeled.

In some embodiments, one or more steps of the method are repeated one or more times such that, e.g., a library of test compounds can be evaluated.

In another aspect, the invention features a method of evaluating a protein, comprising: identifying or selecting a candidate protein, wherein the candidate protein is a polypeptide having acetylation or deacetylation activity, or a cytochrome c polypeptide; altering the sequence, expression or activity of the candidate protein in a cell or in one or more cells of an organism; and determining whether the alteration has an effect on the interaction, e.g., binding, of the polypeptide with a cytochrome c polypeptide, or on the deacetylation of cytochrome c. In one embodiment, the polypeptide has deacetylation activity and is, e.g., a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof.

In some embodiments, the candidate protein is identified by amplification of the gene or a portion thereof encoding the candidate protein, e.g., using a method described herein, e.g., PCR amplification or the screening of a nucleic acid library. In preferred embodiments, the candidate protein is identified by searching a database, e.g., searching a sequence database for protein sequences homologous to the polypeptide or cytochrome c.

In preferred embodiments, the candidate protein is a human protein. In other embodiments, the candidate protein is a mammalian protein, e.g., a mouse protein. In other embodiments, the protein is a vertebrate protein, e.g., a fish, bird or reptile protein, or an invertebrate protein, e.g., a worm or insect protein. In still other embodiments, the protein is a eukaryotic protein, e.g., yeast protein.

In another aspect, the invention features method of evaluating a protein, the method includes: a) identifying or selecting a candidate protein, wherein the candidate protein is a polypeptide having acetylation or deacetylation activity, or a cytochrome c polypeptide; b) identifying one or more polymorphisms in a gene, e.g., one or more SNPs that encodes the candidate protein; and c) assessing correspondence between the presence of one or more of the polymorphisms and an interaction, e.g., binding, of the polypeptide with the cytochrome c, or with the deacetylation of the cytochrome c. In one embodiment, the polypeptide has deacetylation activity and is, e.g., a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof. The polymorphisms can be naturally occurring or laboratory induced. In one embodiment, the organism is an invertebrate, e.g., a fly or nematode; in another embodiment the organism is a mammal, e.g., a rodent or human. A variety of statistical and genetic methods can be used to assess correspondence between a polymorphism and longevity. Such correlative methods include determination of linkage disequilibrium, LOD scores, and the like.

In another aspect, the invention features a method of screening for a compound, e.g., a compound that modulates a polypeptide having acetylation or deacetylation activity to identify agonists or antagonists of the polypeptide. The method includes providing a cell which expresses cytochrome c and which either over- or under-expresses the polypeptide, contacting the cell with a compound; and evaluating the compound for its ability to modulate acetylation in the cell. Acetylation status of cytochrome c can be evaluated and/or cell viability and apoptosis can be evaluated. In some embodiments, the compound can further by evaluated for its effect on mitochondrial function, e.g., respiration.

In some embodiments, when screening for a deacetylation antagonist, the cell can be a cell which over-expresses a polypeptide having deacetylation activity, and the effect of the compound acetylation status of cytochrome c can be evaluated. Possible compounds include, e.g., small organic or inorganic molecules, peptides, antibodies, and nucleic acid molecules. The compound can be evaluated by determining acetylation status of cytochrome c and/or determining cell viability and apoptosis. For example, an antagonist can be selected which reduces programmed cell death and apoptosis of the cell and/or which decrease deacetylation and/or increase acetylation of cytochrome c in the cell. The cell can be, e.g., a cell which includes a sequence encoding the polypeptide under the control of a regulatory sequence, e.g., a regulatory sequence which does not naturally control expression of the polypeptide, e.g., an inducible regulatory sequence, which results in increased levels of the polypeptide being expressed in the cell. In some embodiments, the method is repeated one or more times such that, e.g., a library of test compounds can be evaluated. Such antagonists may be useful, e.g., as candidate compounds for modulating, e.g., decreasing, the rate of aging. These candidate compounds can be evaluated, e.g., by any of the methods described herein to evaluate the rate of aging.

In other embodiments, when screening for a deacetylation agonist, the cell can be a cell which under-expresses a polypeptide having deacetylation activity, and the effect on acetylation status of cytochrome c can be evaluated. Possible compounds include, e.g., small organic and inorganic molecules, peptides, antibodies, and nucleic acid molecules. The compound can be evaluated by determining acetylation status of cytochrome c and/or determining cell viability and apoptosis. For example, an agonist can be selected which increases or induces programmed cell death and apoptosis of the cell and/or which increase deacetylation and/or decrease acetylation in the cell. The cell can be, e.g., a cell which includes a sequence encoding the polypeptide under the control of a regulatory sequence, e.g., a regulatory sequence which does not naturally control expression of the polypeptide, e.g., an inducible regulatory sequence, which results in decreased levels of the polypeptide being expressed in the cell. In other embodiments, the cells can under-express the polypeptide due to an agent which decreases expression of the polypeptide, e.g., antisense, and/or RNAi. In some embodiments, the method is repeated one or more times such that, e.g., a library of test compounds can be evaluated. Such agonists may be useful, e.g., as candidate compounds for aging related disorders and senescence related disorders. These agonist may also be useful, e.g., as candidates, for treating or preventing unwanted cell growth, e.g., cancer, inflammatory and autoimmune disorders, Alzheimer's disease. These candidate compounds can be evaluated, e.g., by any of the methods described herein to evaluate the rate of aging or effect on unwanted cell proliferation.

In one embodiment, the polypeptide has deacetylation activity and is, e.g., a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof. In some embodiments, when screening for a SIR antagonist, the cell can be a cell which over-expresses a SIR polypeptide, and the effect of the compound on SIR expression and/or activity can be evaluated. Possible compounds include, e.g., small organic or non-organic molecules, peptides, antibodies, and nucleic acid molecules. In one embodiment, the expression levels of the SIR polypeptide prior to and after administration of a compound to the cell can be evaluated, and compounds which decrease the expression level of the SIR polypeptide can be selected as SIR antagonists. A decrease in the expression level is any statistically significant decrease in a SIR polypeptide expression levels. In some preferred embodiments, SIR antagonist are selected which result in SIR expression levels in the over-expressing cell to return to levels comparable to the same cell type but which has not been modified to increase SIR levels. In other embodiments, the cell can be a cell which over-expresses a SIR polypeptide, and compounds which decrease SIR expression and effect an activity can be evaluated for their effect on a SIR activity, e.g., apoptosis and/or deacetylation. For example, SIR antagonist can be selected which reduces programmed cell death and apoptosis of the cell and/or which decrease deacetylation and/or increase acetylation in the cell. The cell can be, e.g., a cell which includes a SIR encoding sequence under the control of a regulatory sequence, e.g., a non-SIR regulatory sequence, e.g., an inducible regulatory sequence, which results in increased levels of SIR being expressed in the cell. Such antagonists may be useful, e.g., as candidate compounds for modulating, e.g., decreasing, the rate of aging. These candidate compounds can be evaluated, e.g., by any of the methods described herein to evaluate the rate of aging.

In other embodiments, when screening for a SIR agonist, the cell can be a cell which under-expresses a SIR polypeptide, and the effect of the compound on SIR expression and/or activity can be evaluated. Possible compounds include, e.g., small organic or inorganic molecules, peptides, antibodies, and nucleic acid molecules. In one embodiment, the expression levels of SIR prior to and after administration of a compound to the cell can be evaluated, and compounds which increase the expression level of SIR can be selected as SIR agonists. An increase in the expression level is any statistically significant increase in SIR expression levels. In some preferred embodiments, SIR agonist are selected which result in SIR expression levels in the under expressing cell to return to levels comparable to the same, cell type but which has not been modified to reduce SIR levels. In other embodiments, the cell can be a cell which under-expresses SIR, and compounds which increase SIR expression and activity can be evaluated for their effect on a SIR activity, e.g., apoptosis and/or deacetylation. For example, SIR agonist can be selected which increases or induces programmed cell death and apoptosis of the cell and/or which increase deacetylation and/or decrease acetylation in the cell. The cell can be, e.g., a cell which includes a SIR encoding sequence under the control of a regulatory sequence, e.g., a non-SIR regulatory sequence, e.g., an inducible regulatory sequence, which results in decreased levels of SIR being expressed in the cell. In other embodiments, the cells can under-express SIR due to an agent which decreases SIR expression, e.g., a SIR antisense, RNAi. In some embodiments, the method is repeated one or more times such that, e.g., a library of test compounds can be evaluated. Such agonists may be useful, e.g., as candidate compounds for aging related disorders and senescence related disorders. These agonist may also be useful, e.g., as candidates, for treating or preventing unwanted cell growth, e.g., cancer, inflammatory and autoimmune disorders, Alzheimer's disease. These candidate compounds can be evaluated, e.g., by any of the methods described herein to evaluate the rate of aging or effect on unwanted cell proliferation.

In another aspect, the invention features a method of modulating cell growth in an animal, e.g., a mammal, by modulating the acetylation status of a cytochrome c in the animal. In some embodiments, cell growth can be modulated using an antagonist or agonist of deacetylation. For example, in some embodiments, an antagonist or agonist of a SIR polypeptide, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, can be used.

In one embodiment, the method includes modulating cell growth by increasing acetylation of cytochrome c. An increase in acetylation of cytochrome c can reduce or inhibit apoptosis of a cell. In a further embodiment, the method includes inactivating a polypeptide having deacetylation activity, e.g., by the use of antisense, RNAi, antibodies, intrabodies, NAD depletion, a dominant negative mutant of the polypeptide, or by the addition of cofactor-analogs, e.g., NAD analogs such as those described in Vaziri et al. (1997) or nicotinamide. In a further embodiment, the method includes introducing a deacetylation-resistant form of cytochrome c.

In another embodiment, the method includes modulating cell growth by decreasing acetylation of cytochrome c. A decrease in acetylation of cytochrome c can increase or induce apoptosis in a cell. In a further embodiment, the method includes increasing NAD concentrations. In a further embodiment, the method includes increasing concentrations of a polypeptide having deacetylation activity, e.g. by addition of purified polypeptide, by expression of the polypeptide from heterologous genes, or by increasing the expression of endogenous polypeptide, or by the addition of cofactor-analogs, e.g., NAD analogs such as those described in Vaziri et al. (1997). In still another embodiment, the invention is a method for treating a mammal, e.g., a mammal having a disease characterized by unwanted cell proliferation, e.g., cancer, accelerated senescence-related disorders, inflammatory and autoimmune disorders, Alzheimer's disease, and aging-related disorders, e.g., a human mammal. The method can also be used to treat a disorder described in Ser. Nos. 10/656,530 or 60/488,261.

The present invention also relates to a method of modulating the growth of a cell in vivo or in vitro by modulating the deacetylation of a cytochrome c in the cell.

In one embodiment, the method includes modulating the growth of a cell by increasing acetylation of cytochrome c, thereby increasing cell growth. In a further embodiment, the method includes inactivating a polypeptide having deacetylation activity, e.g., by the use of antisense, RNAi, antibodies, intrabodies, NAD depletion, a dominant negative mutant of the polypeptide, or nicotinamide, or decreasing the polypeptide's activity by the addition of cofactor-analogs, e.g., NAD analogs such as those described in Vaziri et al. (1997). In a further embodiment, the method includes introducing a deacetylation-resistant form of cytochrome c. In one embodiment, the polypeptide is a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof.

In one embodiment, the method includes modulating the growth of a cell by decreasing acetylation of cytochrome c, thereby affecting cell growth. In a further embodiment, the method includes increasing NAD concentrations. In a further embodiment, the method includes increasing concentrations of a polypeptide having deacetylation activity, e.g. by addition of purified polypeptide, by expression of the polypeptide from heterologous genes, or by increasing the expression of endogenous sequence encoding the polypeptide, or by the addition of cofactor-analogs, e.g., NAD analogs such as those described in Vaziri et al. (1997) and U.S. 2003/0207325 (Ser. No. 09/461,580).

In another aspect, the invention is a method for treating or preventing a disease characterized by unwanted cell proliferation, e.g., cancer, in a subject. The method includes administering a deacetylation agonist. For example, the agonist can be one or more of: a purified polypeptide having deacetylation activity, by expression of such a polypeptide from heterologous genes, or by increasing the expression of an endogenous sequence encoding such a polypeptide, and other compounds identified by a method described herein, e.g., compounds that induce apoptosis in a cell, e.g., a cell expressing a polypeptide having deacetylation activity. In one embodiment, the polypeptide a SIR polypeptide. Preferably, the SIR polypeptide is, e.g., a SIRT1 polypeptide, a SIRT2 polypeptide, a SIRT3 polypeptide, a SIRT4 polypeptide, a SIRT5 polypeptide, a SIRT6 polypeptide, a SIRT7 polypeptide, or combinations thereof.

In a preferred embodiment, the method includes administering a deacetylation agonist in combination with one or more therapeutic agents, e.g., a therapeutic agent or agent for treating unwanted cell proliferation. The therapeutic agents include, for example, one or more of a chemotherapeutic agent, a radioisotope, and a cytotoxin. Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids). Radioisotopes can include alpha, beta and/or gamma emitters. Examples of radioisotopes include $^{212}$Bi $^{213}$Bi, $^{131}$I, $^{211}$At, $^{186}$Re, $^{90}$Y and $^{117}$Lu.

The agonist and the therapeutic agents can be administered simultaneously or sequentially.

The subject can be a human subject or a non-human subject, e.g., an animal model.

In another aspect, the invention features a method of treating or preventing a disease or disorder. The method includes modulating cytochrome c deacetylation activity of a SIR polypeptide in a subject, e.g., by providing a modulator of SIR cytochrome c deacetylation activity to the subject. The modulator can be provided by administering the modulator to the subject, or, e.g., by an ex vivo method in which cells of the subject or of another organism are contacted with the modulator and then administered to the subject. Exemplary modulators include compounds that alter binding or access to an active site of a SIR polypeptide (e.g., an antibody or NAD analog, e.g., nicotinamide), compounds that alter the expression level of a SIR polypeptide, component (e.g., RNAi, siRNAs, antisense, a nucleic acids encoding a SIR polypeptide), and other compounds, e.g., as described herein.

In one embodiment, the modulator can be provided to a subject who has or is predisposed to having an age-associated disorder. An "age-associated disorder" or "age-related disorder" is a disease or disorder whose incidence is at least 1.5 fold higher among human individuals greater than 60 years of age relative to human individuals between the ages of 30-40, at the time of filing of this application and in a selected population of greater than 100,000 individuals. A preferred population is a United States population. A population can be restricted by gender and/or ethnicity.

In one embodiment, the method includes, e.g., before, during or after the providing, evaluating cells of the subject for cytochrome c, e.g., acetylation state of cytochrome c. The results can be compared to reference results, e.g., from a normal subject or from the subject at a different time. The cells that are evaluated can be in a sample from the subject. For example, the cells can be blood cells, muscle cells, or fibroblasts (e.g., using a cheek swab, etc.).

In one embodiment, the modulator can be provided to a subject who has or is predisposed to having a geriatric disorder. A "geriatric disorder" is a disease or disorder whose incidence, at the time of filing of this application and in a selected population of greater than 100,000 individuals, is at least 70% among human individuals that are greater than 70 years of age. In one embodiment, the geriatric disorder is a disorder other than cancer or a cardio-pulmonary disorder. A preferred population is a United States population. A population can be restricted by gender and/or ethnicity.

In one embodiment, the modulator can be provided to a subject who has or is predisposed to having a disorder having an age-associated susceptibility factor. A disorder having an "age-associated susceptibility factor" refers to a disease or disorder whose causation is mediated by an externality, but whose severity or symptoms are substantially increased in human individuals over the age of 60 relative to human individuals between the ages of 30-40, at the time of filing of this application and in the United States population. For example, pneumonia is caused by pathogens, but the severity of the disease is greater in humans over the age of 60 relative to human individuals between the ages of 30-40.

In one embodiment, the modulator can be provided to a subject who has or is predisposed to having a neoplastic disorder or an age-associated neoplastic disorder. A "neoplastic disorder" is a disease or disorder characterized by cells that have the capacity for autonomous growth or replication, e.g., an abnormal state or condition characterized by proliferative cell growth. An "age-associated neoplastic disorder" is a neoplastic disorder that is also an age-associated disorder.

In one embodiment, the modulator can be provided to a subject who has or is predisposed to having a non-neoplastic disorder or an age-associated non-neoplastic disorder. A "non-neoplastic disorder" is a disease or disorder that is not characterized by cells that have the capacity for autonomous growth or replication. An "age-associated non-neoplastic disorder" is a non-neoplastic disorder that is also an age-associated disorder.

In one embodiment, the modulator can be provided to a subject who has or is predisposed to having a neurological disorder or an age-associated neurological disorder. A "neurological disorder" is a disease or disorder characterized by an abnormality or malfunction of neuronal cells or neuronal support cells (e.g., glia or muscle). The disease or disorder can affect the central and/or peripheral nervous system. Exemplary neurological disorders include neuropathies, skeletal muscle atrophy, and neurodegenerative diseases, e.g., a neurodegenerative disease caused at least in part by polyglutamine aggregation. Exemplary neurodegenerative diseases include: Alzheimer's, Amyotrophic Lateral Sclerosis (ALS), and Parkinson's disease. An "age-associated neurological disorder is a neurological disorder that is also an age-associated disorder.

In one embodiment, the modulator can be provided to a subject who has or is predisposed to having a cardiovascular disorder or an age-associated cardiovascular disorder. A "cardiovascular disorder" is a disease or disorder characterized by an abnormality or malfunction of the cardiovascular system, e.g., heart, lung, or blood vessels. Exemplary cardiovascular disorders include: cardiac dysrhythmias, chronic congestive heart failure, ischemic stroke, coronary artery disease and cardiomyopathy. An "age-associated cardiovascular disorder is a cardiovascular disorder that is also an age-associated disorder.

In one embodiment, the modulator can be provided to a subject who has or is predisposed to having a metabolic disorder or an age-associated metabolic disorder. A "metabolic disorder" is a disease or disorder characterized by an abnormality or malfunction of metabolism. One category of metabolic disorders are disorders of glucose or insulin metabolism An "age-associated metabolic disorder is a metabolic disorder that is also an age-associated disorder.

In one embodiment, the modulator can be provided to a subject who has or is predisposed to having a dermatological disorder, a dermatological tissue condition, or an age-associated dermatological disorder or tissue condition. A "dermatological disorder" is a disease or disorder characterized by an abnormality or malfunction of the skin. A "dermatological tissue condition" refers to the skin and any underlying tissue (e.g., support tissue) which contributes to the skins function and/or appearance, e.g., cosmetic appearance.

Exemplary diseases and disorders that are relevant to certain implementations include: cancer (e.g., breast cancer, colorectal cancer, CCL, CML, prostate cancer); skeletal muscle atrophy; adult-onset diabetes; diabetic nephropathy, neuropathy (e.g., sensory neuropathy, autonomic neuropathy, motor neuropathy, retinopathy); obesity; bone resorption; age-related macular degeneration, ALS, Alzheimer's, Bell's Palsy, atherosclerosis, cardiovascular disorders (e.g., cardiac dysrhythmias, chronic congestive heart failure, ischemic stroke, coronary artery disease and cardiomyopathy), chronic renal failure, type 2 diabetes, ulceration, cataract, presbiopia, glomerulonephritis, Guillan-Barre syndrome, hemorrhagic stroke, short-term and long-term memory loss, rheumatoid arthritis, inflammatory bowel disease, multiple sclerosis, SLE, Crohn's disease, osteoarthritis, Parkinson's disease, pneumonia, and urinary incontinence. In addition, many neurodegenerative disorders and disorders associated with protein aggregation (e.g., other than polyglutamine aggregation) or protein misfolding can also be age-related. Symptoms and diagnosis of diseases are well known to medical practitioners. The compositions may also be administered to individuals being treated by other means for such diseases, for example, individuals being treated with a chemotherapeutic (e.g., and having neutropenia, atrophy, cachexia, nephropathy, neuropathy) or an elective surgery.

Definitions

A Sir protein, derivative, and functional domains thereof are collectively referred to as "SIR polypeptides" or "SIR proteins". "SIR proteins" and "SIR polypeptides" are used interchangeably herein and refer to members of the Silent Information Regulator (SIR) 2 family of genes. The SIR family includes SIRT1, SIRT2, SIRT3, SIRT4, SIRT5, SIRT6, and SIRT7. The term "SIRT1 proteins" or "SIRT1 polypeptides" refers to a polypeptide that is at least 25% identical to the 250 amino acid conserved SIRT1 catalytic domain, amino acid residues 258 to 451 of SEQ ID NO:2. SEQ ID NO: 1 depicts the amino acid sequence of human SIRT1. In preferred embodiments, a SIRT1 polypeptide can be at least 30, 40, 50, 60, 70, 80, 85, 90, 95, 99% homologous to SEQ ID NO:1. In other embodiments, the SIRT1 polypeptide can be a fragment, e.g., a fragment of SIRT1 capable of one or more of: deacetylating a substrate in the presence of NAD and/or a NAD analog and capable of binding a target protein, e.g., a cytochrome c. Such functions can be evaluated, e.g., by the methods described herein. The term "SIRT2 proteins" or "SIRT2 polypeptides" refers to a polypeptide at least 30, 40, 50, 60, 70, 80, 85, 90, 95, 99% homologous to SEQ ID NO:2. SEQ ID NO:2 depicts the amino acid sequence of human SIRT2. In other embodiments, the SIRT2 polypeptide can be a fragment, e.g., a fragment of SIRT2 capable of one or more of: deacetylating a substrate in the presence of NAD and/or a NAD analog and capable of binding a target protein, e.g., a cytochrome c. Such functions can be evaluated, e.g., by the methods described herein. The term "SIRT3 proteins" or "SIRT3 polypeptides" refers to a polypeptide at least 30, 40, 50, 60, 70, 80, 85, 90, 95, 99% homologous to SEQ ID NO:3. SEQ ID NO:3 depicts the amino acid sequence of human SIRT3. In other embodiments, the SIRT3 polypeptide can be a fragment, e.g., a fragment of SIRT3 capable of one or more of: deacetylating a substrate in the presence of NAD and/or a NAD analog and capable of binding a target protein, e.g., a cytochrome c. Such functions can be evaluated, e.g., by the methods described herein. The term "SIRT4 proteins" or "SIRT4 polypeptides" refers to a polypeptide at least 30, 40, 50, 60, 70, 80, 85, 90, 95, 99% homologous to SEQ ID NO:4. SEQ ID NO:4 depicts the amino acid sequence of human SIRT4. In other embodiments, the SIRT4 polypeptide can be a fragment, e.g., a fragment of SIRT4 capable of one or more of: deacetylating a substrate in the presence of NAD and/or a NAD analog and capable of binding a target protein, e.g., a cytochrome c. Such functions can be evaluated, e.g., by the methods described herein. The term "SIRT5 proteins" or "SIRT5 polypeptides" refers to a polypeptide at least 30, 40, 50, 60, 70, 80, 85, 90, 95, 99% homologous to SEQ ID NO:5. SEQ ID NO:5 depicts the amino acid sequence of human SIRT5. In other embodiments, the SIRT5 polypeptide can be a fragment, e.g., a fragment of SIRT5 capable of one or more of: deacetylating a substrate in the presence of NAD and/or a NAD analog and capable of binding a target protein, e.g., a cytochrome c. Such functions can be evaluated, e.g., by the methods described herein. The term "SIRT6 proteins" or "SIRT6 polypeptides" refers to a polypeptide at least 30, 40, 50, 60, 70, 80, 85, 90, 95, 99% homologous to SEQ ID NO:6. SEQ ID NO:6 depicts the amino acid sequence of human SIRT6. In other embodiments, the SIRT6 polypeptide can be a fragment, e.g., a fragment of SIRT6 capable of one or more of: deacetylating a substrate in the presence of NAD and/or a NAD analog and capable of binding a target protein, e.g., a cytochrome c. Such functions can be evaluated, e.g., by the methods described herein. The term "SIRT7 proteins" or "SIRT7 polypeptides" refers to a polypeptide at least 30, 40, 50, 60, 70, 80, 85, 90, 95, 99% homologous to SEQ ID NO:7. SEQ ID NO:7 depicts the amino acid sequence of human SIRT7. In other embodiments, the SIRT7 polypeptide can be a fragment, e.g., a fragment of SIRT7 capable of one or more of: deacetylating a substrate in the presence of NAD and/or a NAD analog and capable of binding a target protein, e.g., a cytochrome c. Such functions can be evaluated, e.g., by the methods described herein. The sequences of human SIRT1, SIRT2, SIRT3, SIRT4 and SIRT5 are also disclosed, e.g., in Frye et al. (1999) Biochem. Biophys. Res. Comm. 260(1):273-279, and the sequences of human SIRT6 and SIRT7 are disclosed, e.g., in Frye et al. (2000) Biochem. Biophys. Res. Comm. 273(2):793-798, the contents of which are incorporated herein by reference. In some embodiments, the SIR polypeptide can be a "full length" SIR polypeptide. The term "full length" as used herein refers to a polypeptide that has at least the length of a naturally occurring SIR polypeptide (or other protein described herein). A "full length" SIR polypeptide or a fragment thereof can also include other sequences, e.g., a purification tag., or other attached compounds, e.g., an attached fluorophore, or cofactor. The term "SIR polypeptides" can also include sequences or variants that include one or more substitutions, e.g., between one and ten substitutions, with respect to a naturally occurring Sir2 family member. In preferred embodiments, a human SIR polypeptide can vary from SEQ ID NO:1, 2, 3, 4, 5, 6, or 7 by at least 1, 2, 3, 4, 5, 10, 15, but preferably not more than 20 to 50 amino acid residues, e.g., it can vary by at least 1, 2, 3, 4, 5, 10, 15 substitutions, e.g., conservative substitutions. In one embodiment, the variation is a naturally occurring variation. In other embodiments, the SIR polypeptide is encoded by a nucleic acid which hybridizes under stringent conditions to a nucleic acid encoding the amino acid sequence of SEQ ID NO:1, 2, 3, 4, 5, 6, or 7. This application also incorporates by reference U.S. Ser. No. 10/191,121, for all purposes. This application also includes a listing of exemplary SIR sequences.

The following are exemplary SIR sequences:

>sp|Q96EB6|SIR1_HUMAN NAD-dependent deacetylase sirtuin 1
(EC 3.5.1.-) (hSIRT1) (hSIR2) (SIR2-like protein 1) - Homo
sapiens (Human).
(SEQ ID NO:1)
MADEAALALQPGGSPSAAGADREAASSPAGEPLRKRPRRDGPGLERSPGEPGGAAPEREV
PAAARGCPGAAAAALWREAEAEAAAAGGEQEAQATAAAGEGDNGPGLQGPSREPPLADNL
YDEDDDDEGEEEEEAAAAAIGYRDNLLFGDEIITNGFHSCESDEEDRASHASSSDWTPRP
RIGPYTFVQQHLMIGTDPRTILKDLLPETIPPPELDDMTLWQIVINILSEPPKRKKRKDI
NTIEDAVKLLQECKKIIVLTGAGVSVSCGIPDFRSRDGIYARLAVDFPDLPDPQAMFDIE
YFRKDPRPFFKFAKEIYPGQFQPSLCHKFIALSDKEGKLLRNYTQNIDTLEQVAGIQRII
QCHGSFATASCLICKYKVDCEAVRGDIFNQVVPRCPRCPADEPLAIMKPEIVFFGENLPE
QFHRAMKYDKDEVDLLIVIGSSLKVRPVALIPSSIPHEVPQILINREPLPHLHFDVELLG
DCDVIINELCHRLGGEYAKLCCNPVKLSEITEKPPRTQKELAYLSELPPTPLHVSEDSSS
PERTSPPDSSVIVTLLDQAAKSNDDLDVSESKGCMEEKPQEVQTSRNVESIAEQMENPDL
KNVGSSTGEKNERTSVAGTVRKCWPNRVAKEQISRRLDGNQYLFLPPNRYIFHGAEVYSD
SEDDVLSSSSCGSNSDSGTCQSPSLEEPMEDESEIEEFYNGLEDEPDVPERAGGAGFGTD
GDDQEAINEAISVKQEVTDMNYPSNKS >sp|Q8IXJ6|SIR2_HUMAN NAD-dependent deacetylase sirtuin 2
(EC 3.5.1.-) (SIR2-like) (SIR2- like protein 2) - Homo
sapiens (Human).
(SEQ ID NO:2)
MAEPDPSHPLETQAGKVQEAQDSDSDSEGGAAGGEADMDFLRNLFSQTLSLGSQKERLLD
ELTLEGVARYMQSERCRRVICLVGAGISTSAGIPDFRSPSTGLYDNLEKYHLPYPEAIFE
ISYFKKHPEPFFALAKELYPGQFKPTICHYFMRLLKDKGLLLRCYTQNIDTLERIAGLEQ
EDLVEAHGTFYTSHCVSASCRHEYPLSWMKEKIFSEVTPKCEDCQSLVKPDIVFFGESLP
ARFFSCMQSDFLKVDLLLVMGTSLQVQPFASLISKAPLSTPRLLINKEKAGQSDPFLGMI
MGLGGGMDFDSKKAYRDVAWLGECDQGCLALAELLGWKKELEDLVRREHASIDAQSGAGV
PNPSTSASPKKSPPPAKDEARTTEREKPQ >sp|Q9NTG7|SIR3_HUMAN NAD-dependent deacetylase sirtuin 3,
mitochondrial precursor (EC 3.5.1.-) (SIR2-like protein 3)
(hSIRT3) - Homo sapiens (Human).
(SEQ ID NO:3)
MAFWGWRAAAALRLWGRVVERVEAGGGVGPFQACGCRLVLGGRDDVSAGLRGSHGARGEP
LDPARPLQRPPRPEVPRAFRRQPRAAAPSFFFSSIKGGRRSISFSVGASSVVGSGGSSDK
GKLSLQDVAELIRARACQRVVVMVGAGISTPSGIPDFRSPGSGLYSNLQQYDLPYPEAIF
ELPFFFHNPKPFFTLAKELYPGNYKPNVTHYFLRLLHDKGLLLRLYTQNIDGLERVSGIP
ASKLVEAHGTFASATCTVCQRPFPGEDIRADVMADRVPRCPVCTGVVKPDIVFFGEPLPQ
RFLLHVVDFPMADLLLILGTSLEVEPFASLTEAVRSSVPRLLINRDLVGPLAWHPRSRDV
AQLGDVVHGVESLVELLGWTEEMRDLVQRETGKLDGPDK >sP|Q9Y6E7|SIR4_HUMAN NAD-dependent deacetylase sirtuin 4
(EC 3.5.1.-) (SIR2-like protein 4) - Homo sapiens (Human).
(SEQ ID NO:4)
MKMSFALTFRSAKGRWIANPSQPCSKASIGLFVPASPPLDPEKVKELQRFITLSKRLLVM
TGAGISTESGIPDYRSEKVGLYARTDRRPIQHGDFVRSAPIRQRYWARNFVGWPQFSSHQ
PNPAHWALSTWEKLGKLYWLVTQNVDALHTKAGSRRLTELHGCMDRVLCLDCGEQTPRGV
LQERFQVLNPTWSAEAHGLAPDGDVFLSEEQVRSFQVPTCVQCGGHLKPDVVFFGDTVNP
DKVDFVHKRVKEADSLLVVGSSLQVYSGYRFILTAWEKKLPIAILNIGPTRSDDLACLKL
NSRCGELLPLIDPC >sp|Q9NXA8|SIR5_HUMAN NAD-dependent deacetylase sirtuin 5
(EC 3.5.1.-) (SIR2-like protein 5) - Homo sapiens (Human).
(SEQ ID NO:5)
MRPLQIVPSRLISQLYCGLKPPASTRNQICLKMARPSSSMADFRKFFAKAKHIVIISGAG
VSAESGVPTFRGAGGYWRKWQAQDLATPLAFAHNPSRVWEFYHYRREVMGSKEPNAGHRA
IAECETRLGKQGRRVVVITQNIDELHRKAGTKNLLEIHGSLFKTRCTSCGVVAENYKSPI
CPALSGKGAPEPGTQDASIPVEKLPRCEEAGCGGLLRPHVVWFGENLDPAILEEVDRELA
HCDLCLVVGTSSVVYPAAMFAPQVAARGVPVAEFNTETTPATNRFRFHFQGPCGTTLPEA
LACHENETVS >sp |Q8N6T7|SIR6_HUMAN NAD-dependent deacetylase sirtuin 6
(EC 3.5.1.-) (SIR2-like protein 6) - Homo sapiens (Human).
(SEQ ID NO:6)
MSVNYAAGLSPYADKGKCGLPEIFDPPEELERKVWELARLVWQSSSVVFHTGAGISTASG
IPDFRGPHGVWTMEERGLAPKFDTTFESARPTQTHMALVQLERVGLLRFLVSQNVDGLHV
RSGFPRDKLAELHGNMFVEECAKCKTQYVRDTVVGTMGLKATGRLCTVAKARGLRACRGE
LRDTILDWEDSLPDRDLALADEASRNADLSITLGTSLQIRPSGNLPLATKRRGGRLVIVN
LQPTKHDRHADLRIHGYVDEVMTRLMKHLGLEIPAWDGPRVLERALPPLRPPTPKLEPK
EESPTRINGSIPAGPKQEPCAQHNGSEPASPKRERPTSPAPHRPPKRVKAKAVPS -continued >sp|Q9NRC8|SIR7_HUMAN NAD-dependent deacetylase sirtuin 7
(EC 3.5.1.-) (SIR2-like protein 7) - Homo sapiens (Human).
(SEQ ID NO:7)
MAAGGLSRSERKAAERVRRLREEQQRERLRQVSRILRKAAAERSAEEGRLLAESADLVTE
LQGRSRRREGLKRRQEEVCDDPEELRGKVRELASAVRNAKYLVVYTGAGISTAASIPDYR
GPNGVWTLLQKGRSVSAADLSEAEPTLTHMSITRLHEQKLVQHVVSQNCDGLHLRSGLPR
TAISELHGNMYIEVCTSCVPNREYVRVFDVTERTALHRHQTGRTCHKCGTQLRDTIVHFG
ERGTLGQPLNWEAATEAASRADTILCLGSSLKVLKKYPRLWCMTKPPSRRPKLYIVNLQW
TPKDDWAALKLHGKCDDVMRLLMAELGLEIPAYSRWQDPIFSLATPLRAGEEGSHSRKSL
CRSREEAPPGDRGAPLSSAPILGGWFGRGCTKRTKRKKVT The term "SIR polypeptide" also includes homologs of the various human SIR polypeptides from other species, e.g., other mammalian species, including the murine homologs. A "SIR activity" refers to one or more activity of a SIR polypeptide, e.g., deacetylation of a substrate, e.g., cytochrome c, (e.g., in the presence of a cofactor such as NAD and/or an NAD analog) and binding of a target protein, e.g., cytochrome c or a nuclear protein, e.g., a transcription factor.

As used herein, the term "nucleic acid molecule" includes DNA molecules (e.g., a cDNA or genomic DNA), RNA molecules (e.g., an mRNA) and analogs of the DNA or RNA. A DNA or RNA analog can be synthesized from nucleotide analogs. The nucleic acid molecule can be single-stranded or double-stranded, e.g., double-stranded DNA or a double-stranded RNA. Nucleic acid molecules encoding the SIR polypeptides or proteins are collectively referred to as "SIR nucleic acids". Such nucleic acids include naturally occurring genomic and cDNA sequences, naturally occurring variants, and synthetic sequences (e.g., codon-optimized coding sequences). The polypeptide may include one or more unnatural amino acids. Typically, the polypeptide includes only natural amino acids. The term "peptide" refers to a polypeptide that is between three and thirty-two amino acids in length. A protein or polypeptide can also include one or more modifications, e.g., a glycosylation, amidation, phosphorylation, and so forth.

The term "isolated nucleic acid molecule" or "purified nucleic acid molecule" includes nucleic acid molecules that are separated from other nucleic acid molecules present in the natural source of the nucleic acid. For example, with regards to genomic DNA, the term "isolated" includes nucleic acid molecules which are separated from the chromosome with which the genomic DNA is naturally associated. In some embodiments, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Examples of flanking sequences include adjacent genes, transposons, and regulatory sequences. Moreover, an "isolated" nucleic acid molecule, such as a cDNA molecule, can be substantially free of other cellular material, of culture medium when produced by recombinant techniques, or of chemical precursors or other chemicals when chemically synthesized.

As used herein, the term "hybridizes under low stringency, medium stringency, high stringency, or very high stringency conditions" describes conditions for hybridization and washing. Guidance for performing hybridization reactions can be found in *Current Protocols in Molecular Biology*, John Wiley Sons, N.Y. (1989), 6.3.1-6.3.6, which is incorporated by reference. Aqueous and nonaqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.2× SSC, 0.1% SDS at least at 50° C. (the temperature of the washes can be increased to 55° C. for low stringency conditions); 2) medium stringency hybridization conditions in 6×SSC at about 45° C., followed by one or more washes in 0.2×SSC, 0.1% SDS at 60° C.; 3) high stringency hybridization conditions in 6×SSC at about 45° C., followed by one or more washes in 0.2×SSC, 0.1% SDS at 65° C.; and preferably 4) very high stringency hybridization conditions are 0.5 M sodium phosphate, 7% SDS at 65° C., followed by one or more washes at 0.2×SSC, 1% SDS at 65° C. Very high stringency conditions (4) are the preferred conditions and the ones that should be used unless otherwise specified. Methods of the invention can include use of an isolated nucleic acid molecule of the invention that hybridizes under a stringency condition described herein to a sequence described herein or use of a polypeptide encoded by such a sequence, e.g., the molecule can be a naturally occurring variant.

As used herein, a "naturally-occurring" nucleic acid molecule refers to an RNA or DNA molecule having a nucleotide sequence that occurs in Nature. For example a naturally occurring nucleic acid molecule can encode a natural protein.

As used herein, the terms "gene" and "recombinant gene" refer to nucleic acid molecules which include at least an open reading frame encoding a protein or subunit, derivative, or functional domain thereof. The gene can optionally further include non-coding sequences, e.g., regulatory sequences and introns.

An "isolated" or "purified" polypeptide or protein is substantially free of cellular material or other contaminating proteins from the cell or tissue source from which the protein is derived, or substantially free from chemical precursors or other chemicals when chemically synthesized. "Substantially free" means that the protein of interest in the preparation is at least 10% pure. In an embodiment, the preparation of the protein has less than about 30%, 20%, 10% and more preferably 5% (by dry weight), of a contaminating component (e.g., a protein not of interest, chemical precursors, and so forth). When the protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of protein without abolishing or substantially altering activity, e.g., the activity is at least 20%, 40%, 60%, 70% or 80% of wild-type. An "essential" amino acid residue is a residue that, when altered from the wild-type sequence results in abolishing activity such that less than 20% of the wild-type activity is present. Conserved amino acid residues are frequently predicted to be particularly unamenable to alteration.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a protein is preferably replaced with another amino acid residue from the same side chain family. Alternatively, in another embodiment, mutations can be introduced randomly along all or part of a coding sequence, such as by saturation mutagenesis, and the resultant mutants can be screened for biological activity to identify mutants that retain activity. Following mutagenesis, the encoded protein can be expressed recombinantly and the activity of the protein can be determined.

As used herein, a "biologically active portion" or a "functional domain" of a protein includes a fragment of a protein of interest which participates in an interaction, e.g., an intramolecular or an inter-molecular interaction, e.g., a binding or catalytic interaction. An inter-molecular interaction can be a specific binding interaction or an enzymatic interaction (e.g., the interaction can be transient and a covalent bond is formed or broken). An inter-molecular interaction can be between the protein and another protein, between the protein and another compound, or between a first molecule and a second molecule of the protein (e.g., a dimerization interaction). Biologically active portions/functional domains of a protein include peptides comprising amino acid sequences sufficiently homologous to or derived from the amino acid sequence of the protein which include fewer amino acids than the full length, natural protein, and exhibit at least one activity of the natural protein. Biological active portions/functional domains can be identified by a variety of techniques including truncation analysis, site-directed mutagenesis, and proteolysis. Mutants or proteolytic fragments can be assayed for activity by an appropriate biochemical or biological (e.g., genetic) assay. In some embodiments, a functional domain is independently folded. Typically, biologically active portions comprise a domain or motif with at least one activity of the protein, e.g., a SIR core catalytic domain. A biologically active portion/functional domain of a protein can be a polypeptide which is, for example, 10, 25, 50, 100, 200 or more amino acids in length. Biologically active portions/functional domain of a protein can be used as targets for developing agents which modulate apoptosis.

A variety of methods can be used to identify a SIR family member. For example, a known amino acid sequence of a human SIR polypeptide, e.g., any of human SIRT1, SIRT2, SIRT3, SIRT4, SIRT5, SIRT6, or SIRT7 can be searched against the GenBank sequence databases (National Center for Biotechnology Information, National Institutes of Health, Bethesda Md.), e.g., using BLAST; against Pfam database of HMMs (Hidden Markov Models) (using default parameters for Pfam searching; against the SMART database; or against the ProDom database. For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405-420 and a detailed description of HMMs can be found, for example, in Gribskov et al. (1990) *Meth. Enzymol.* 183:146-159; Gribskov et al. (1987) *Proc. Natl. Acad. Sci. USA* 84:4355-4358; Krogh et al. (1994) *J. Mol. Biol.* 235:1501-1531; and Stultz et al. (1993) *Protein Sci.* 2:305-314. The SMART database (Simple Modular Architecture Research Tool, EMBL, Heidelberg, Del.) of HMMs as described in Schultz et al. (1998), *Proc. Natl. Acad. Sci. USA* 95:5857 and Schultz et al. (200) *Nucl. Acids Res* 28:231. The SMART database contains domains identified by profiling with the hidden Markov models of the HMMer2 search program (R. Durbin et al. (1998) *Biological sequence analysis: probabilistic models of proteins and nucleic acids.* Cambridge University Press). The database also is annotated and monitored. The ProDom protein domain database consists of an automatic compilation of homologous domains. (Corpet et al. (1999), *Nucl. Acids Res.* 27:263-267) Current versions of ProDom are built using recursive PSI-BLAST searches (Altschul et al. (1997) *Nucleic Acids Res.* 25:3389-3402; Gouzy et al. (1999) *Computers and Chemistry* 23:333-340.) of the SWISS-PROT 38 and TREMBL protein databases. The database automatically generates a consensus sequence for each domain.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using the NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of Meyers and Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

Some polypeptides of the present invention can have an amino acid sequence substantially identical to an amino acid sequence described herein. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. Methods of the invention can include use of a polypeptide that includes an amino acid sequence that contains a structural domain having at least about 60%, or 65% identity, likely 75% identity, more likely 85%, 90%, 92%, 94%, 95%, 96%, 97%, 98% or 99% identity to a domain of a polypeptide described herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. Methods of the invention can include use of a nucleic acid that includes a region at least about 60%, or 65% identity, likely 75% identity, more likely 85%, 90%. 91%, 92%, 93%, 94%, 95%, 96%, 97%, 98% or 99% identity to a nucleic acid sequence described herein, or use of a protein encoded by such nucleic acid.

A "purified preparation of cells", as used herein, refers to an in vitro preparation of cells. In the case cells from multicellular organisms (e.g., plants and animals), a purified preparation of cells is a subset of cells obtained from the organism, not the entire intact organism. In the case of unicellular microorganisms (e.g., cultured cells and microbial cells), it consists of a preparation of at least 10% and more preferably 50% of the subject cells.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "small organic molecule" is an organic molecule of having a molecular weight of less than 5, 2, 1, or 0.5 kDa. In many embodiments, such small molecules do not include a peptide bond or a phosphodiester bond. For example, they can be non-polymeric. In some embodiments, the molecule has a molecular weight of at least 50, 100, 200, or 400 Daltons.

"Binding affinity" refers to the apparent dissociation constant or $K_D$. A ligand may, for example, have a binding affinity of at least $10^{-5}$, $10^{-6}$, $10^{-7}$ or $10^{-8}$ M for a particular target molecule. Higher affinity binding of a ligand to a first target relative to a second target can be indicated by a smaller numerical value $K_D^1$ for binding the first target than the numerical value $K_D^2$ for binding the second target. In such cases the ligand has specificity for the first target relative to the second target. The agent may bind specifically to the target, e.g., with an affinity that is at least 2, 5, 10, 100, or 1000 better than for a non-target. For example, an agent can bind to a SIR polypeptide with a $K_d$ of less than $10^{-5}$, $10^{-6}$, $10^{-7}$ or $10^{-8}$ M. If the agent binds specifically, it may be binding to a protein, e.g., to a SIR polypeptide with a $K_d$ of greater than 2, 5, 10, 100, or 1000 times $10^{-5}$, $10^{-6}$, $10^{-7}$ or $10^{-8}$ M, as appropriate.

Binding affinity can be determined by a variety of methods including equilibrium dialysis, equilibrium binding, gel filtration, ELISA, or spectroscopy (e.g., using a fluorescence assay). These techniques can be used to measure the concentration of bound and free ligand as a function of ligand (or target) concentration. The concentration of bound ligand ([Bound]) is related to the concentration of free ligand ([Free]) and the concentration of binding sites for the ligand on the target where (N) is the number of binding sites per target molecule by the following equation:

$$[\text{Bound}] = N \cdot [\text{Free}]/((1/Ka) + [\text{Free}])$$

A "cytochrome c activity" refers to one or more activities of cytochrome c, e.g., cytochrome c mediated apoptosis and/or mitochondrial respiration.

A "cytochrome c polypeptide" refers to a full length cytochrome c or a fragment thereof, e.g., having at least 3 amino acids, e.g., between 3-50, 3-20, 3-15, 3-10, 5-20, 5-12 5-10, or 6-12. An exemplary cytochrome c polypeptide is a human cytochrome c polypeptide which can include the following sequence or a fragment thereof:

(SEQ ID NO:8)
GDVEKGKKIF IMKCSQCHTV EKGGKHKTGP NLHGLFGRKT GQAPGYSYTA

ANKNKGIIWG EDTLMEYLEN PKKYIPGTKM IFVGIKKKEE RADLIAYLKK

ATNE

Exemplary fragments include a lysine. A cytochrome c polypeptide (e.g., full length or a fragment) can be acetylated, e.g., at one or more of the lysines.

One exemplary cytochrome c fragment is able to bind heme. The fragment-heme complex can have spectroscopic properties similar to a full length cytochrome c bound to heme. The fragment-heme complex can be acetylated.

"Modulating cytochrome c activity" refers to increasing or decreasing cytochrome c activity, e.g., cytochrome c-mediated apoptosis, cell cycle arrest, and/or senescence, e.g. by altering the acetylation status of cytochrome c.

The term "chronological age" as used herein refers to time elapsed since a preselected event, such as biological age" as conception, a defined embryological or fetal stage, or, more preferably, birth.

In contrast, the term "biological age" refers to manifestations of the passage of time that is not linearly fixed with the amount of time elapsed. The manifestations of biological aging are varied and may depend on the species of organism, environmental conditions, and, as discussed herein, genotype. Exemplary manifestations of biological aging in mammals include endocrine changes (for example, puberty, menses, changes in fertility or fecundity, menopause, and secondary sex characteristics, such as balding,), metabolic changes (for example, changes in appetite and activity), and immunological changes (for example, changes in resistance to disease). The appearance of mammals also changes with biological age, for example, graying of hair, wrinkling of skin, and so forth. With respect to a different class of animals, the nematode C. elegans also has manifestations of biological aging, for example, changes in fecundity, activity, responsiveness to stimuli, and appearance (e.g., change in intestinal autofluorescence and flaccidity). In many cases, the remaining potential lifespan of an individual is a function of its biological age.

The term "average lifespan" refers to the average of the age of death of a cohort of organisms. In some cases, the "average lifespan" is assessed using a cohort of genetically identical organisms under controlled environmental conditions. Deaths due to mishap are discarded. For example, with respect to a nematode population, hermaphrodites that die as a result of the "bag of worms" phenotype are typically discarded. A variety of criteria can be used to determine whether organisms are of the "same" chronological age for the comparative analysis. Typically, the degree of accuracy required is a function of the average lifespan of a wild type organism. For example, for the nematode C. elegans, for which the laboratory wild type strain N2 lives an average of about 16 days under some controlled conditions, organisms of the same age may have lived for the same number of days. For mice, organism of the same age may have lived for the same number of weeks or months; for primates or humans, the same number of years (or within 2, 3, or 5 years); for Drosophila, the same number of weeks; and so forth.

Other features and advantages of the invention will be apparent from the following detailed description, and from the claims. All patents, patent applications, inclusive of Ser. No. 60/433,096, and references cited herein are incorporated in their entirety by reference.

DETAILED DESCRIPTION OF THE INVENTION

Figure 1:
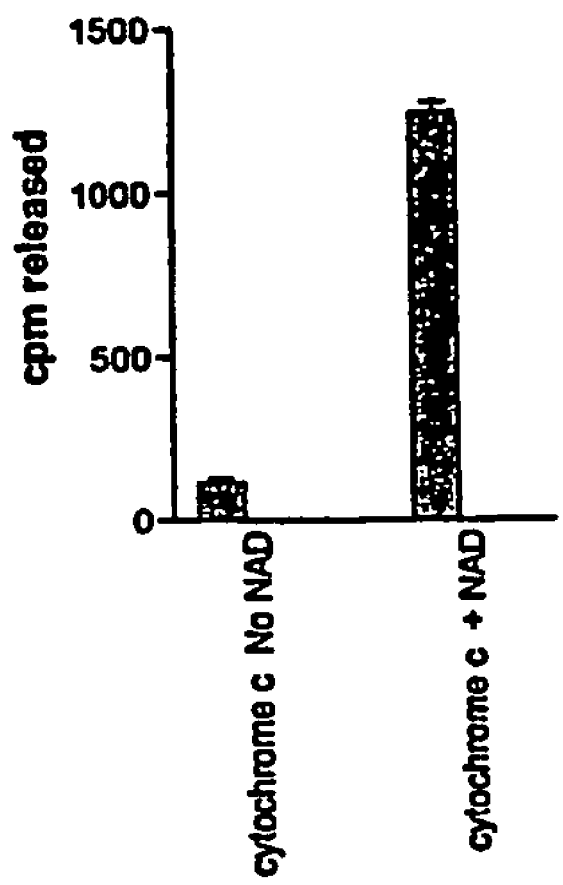
FIG. 1 is a graph showing recombinant GST-SIRT2 deacetylation of acetylated cytochrome c in the presence or absence of NAD.

Control of cytochrome c acetylation, e.g., with a SIR polypeptide, enables interventions that modulate lifespan regulation and cell proliferation, e.g., by modulating apoptosis and/or mitochondrial function such as respiration. Agents which alter lifespan regulation of a cell or organism are identified by screening for compounds that regulate cytochrome c acetylation status, to, e.g., modulate cytochrome c-mediated apoptosis. The agents so-identified and compounds known to alter interaction of cytochrome c and proteins having acetylation or deacetylation activity and/or otherwise alter acetylation status can be administered to a subject, e.g., to alter an apoptotic program or lifespan regulation in the subject or to affect a longevity-associated disorder, or a risk, symptom, predisposition thereof. In other aspects, agents which alter cell proliferation (e.g., decrease cell proliferation) are identified by screening compounds that reduce acetylation of cytochrome c and/or increase cytochrome c-mediated apoptosis.

For example, lifespan regulation can be modulated to enhance, increase, or otherwise favor increased lifespan. A method to increase lifespan can include modulating components of the cytochrome c-mediated apoptosis pathway to: increase acetylation of cytochrome c; decrease interaction, e.g., binding, of a polypeptide having deacetylation activity, e.g., a SIR polypeptide, to cytochrome c; decrease interaction, e.g., binding, between cytochrome c and Apaf-1; and/or decrease cytochrome c-mediated apoptosis of a cell, to thereby favor increased lifespan. Related methods can be used to activate physiological processes in an organism that are associated with an organism of reduced chronological age, e.g., a genetically identical or genetically normal organism of reduced chronological age.

In other aspects, cell proliferation can be modulated to decrease, inhibit or prevent cell proliferation in disorders characterized by unwanted cell proliferation such as cancers.

As described herein, polypeptides having deacetylation activity can interact with human cytochrome c protein to deacetylate cytochrome c. A functional consequence of this deacetylation is an increase of the cytochrome c's interaction with Apaf-1 and its apoptotic activity. Stress on a cell can result in release of cytochrome c from the mitochondria into the cytosol where in its non-acetylated form, it can interact with Apaf-1. Interaction of cytochrome c with Apaf-1 induces events (e.g., the activation of caspases) which can eventually result in apoptosis of the cell. While not wishing to be bound by theory, deacetylation of cytochrome c may enhances cytochrome c's ability to interact with Apaf-1 and induce cytochrome c-mediated apoptotic response. The formation of tumors is a multistep process requiring progressive accumulation of genetic alterations. Thus, cytochrome c release from the mitochondria due to stress, e.g., oncogenic stress, can play an important role in cancer by inducing apoptosis of damaged cells. A consequence of loss of pro apoptotic activity is the accumulation of the half-dozen or so mutations necessary for a cell to become carcinogenic. A second consequence may be uncontrolled cell growth, e.g., metastases, of the cell. In order to enhance or increase cytochrome c mediated apoptosis in these damaged cells, deacetylation of cytochrome c, is, preferably, reduced, inhibited or prevented.

Examples of methods for modulating expression of polypeptides having acetylation or deacetylation activity and/or activity and/or cytochrome c acetylation and/or cytochrome c-mediated apoptotic activity in cells and organisms are described below, as are method of identifying agent which modulate these activities. Many of the screening assays are described with regards to a SIR polypeptide, however, other polypeptides can also be used in the screening assays.

Members of the cytochrome c-mediated apoptotic pathway include polypeptides having deacetylation activity such as Sir polypeptides (e.g., SIRT1, SIRT2, SIRT3, SIRT4, SIRT5, SIRT6, and/or SIRT7 polypeptides), Apaf-1, caspases, such as caspase 9 and caspase 3. The interaction between these members of the cytochrome c-mediated apoptotic pathway is described in detail herein.

Screening Assays

The invention includes methods of screening for a compound, e.g., a compound which interacts with cytochrome c or otherwise effects cytochrome c acetylation status and has an effect on (e.g., induces) apoptosis. Such compounds can be identified as candidates for reducing unwanted cell proliferation in vitro or in vivo (e.g., in a subject having a disorder characterized by unwanted cell proliferation). The method can include providing a compound which interacts with cytochrome c or a polypeptide having acetylation or deacetylation activity and evaluating the effect of the compound on apoptosis. Compounds which interact with cytochrome c or other polypeptides can be identified, e.g., by in vitro or in vivo assays. When both the assay for screening a compound for the ability to interact with cytochrome c or a polypeptide and the assay for determining effect on apoptosis are performed in vivo, e.g., in cell based assays, the assays can be performed in the same or different cells. For example, one or both of the assays can be performed in tissue culture (e.g., BJT cells, 293T cells, MCF-7 cells, H1299 cells) or in an organism (e.g., a mammal, e.g., as a human).

In preferred embodiments, the assays are performed in the presence of a polypeptide cofactor, e.g., a SIR polypeptide co-factor, such as NAD and/or NAD analogs. In some embodiments, the co-factor is added to the cell culture or in vitro assay, e.g., the NAD and/or an NAD analog can be placed in sufficient proximity to cause a SIR polypeptide activity such as deacetylation. "NAD" refers to nicotinamide adenine dinucleotide. An "NAD analog" as used herein refers to a compound (e.g., a synthetic or naturally occurring chemical, drug, protein, peptide, small organic molecule) which possesses structural similarity to component groups of NAD (e.g., adenine, ribose and phosphate groups) or functional similarity (e.g., deacetylates p53 in the presence of Sir2). For example, an NAD analog can be 3-aminobenzamide or 1,3-dihydroisoquinoline (H. Vaziri et al., EMBO J. 16:6018-6033 (1997), the entire teachings of which are hereby incorporated by reference).

Described below are exemplary methods for identifying compounds that interact with cytochrome c and/or a polypeptide having acetylation or deacetylation activity and can have an effect on apoptosis. Preferably, compounds can be identified which interact with, e.g., bind to, cytochrome c or a polypeptide having acetylation or deacetylation activity, and increase acetylation. Deacetylation of a substrate such as cytochrome c has been found to increase substrate-induced apoptosis, e.g., cytochrome c induced apoptosis. Cytochrome c can be, for example, the mature protein or a fragment thereof. In a preferred embodiment, the cytochrome c is human cytochrome c. In many instances, such deacetylated substrates may play a role in apoptosis of stressed and/or damaged cells, e.g., DNA damaged cells, e.g., cancer cells. Thus, in some embodiments, it is desirable to identify compounds which interact with a polypeptide having deacetylation activity and increase expression and or activity of the polypeptide, thereby increasing apoptosis in a cell, e.g., a cancer cell. The phrase "deacetylating a substrate" or "deacetylating cytochrome c" refers to the removal of one or more acetyl groups (e.g., $CH_3CO^{2-}$) from the substrate such as cytochrome c that is acetylated on at least one amino acid residue. Cytochrome c can be deacetylated in the presence or absence of DNA damage or oxidative cellular stress. The DNA damage can be caused by, for example, ionizing radiation (e.g., 6 Gy of ionizing radiation), or a tumor or some other uncontrolled cell proliferation. "Acetylation status" refers to the presence or absence of one or more acetyl groups (e.g., $CH_3CO^{2-}$) at one or more lysine (K) residues of a substrate, e.g., a transcription factor. For example, the presence of an acetylate group can be found at one or more of places of the cytochrome sequence depicted in SEQ ID NO. 8. "Altering the acetylation state" refers to adding or removing one or more acetyl groups (e.g., $CH_3CO^{2-}$). For example, adding or removing one or more acetyl groups of cytochrome c at one or more lysine (K) residues of SEQ ID NO. 8.

A cytochrome c polypeptide can be monitored using a fluorescence assay. For example, an acetylated cytochrome c polypeptide can be used as a substrate and monitored, e.g., as described in U.S. 2003-0082668. For example, the cytochrome c polypeptide can be prepared as a fluorescent substance that includes a fluorescence group and a quencher. Specific examples include MOAc, Nma (N-methylanthranilic acid), etc. Further, a quencher group should have the characteristic to quench the fluorescence of a fluorescent group within the same peptide molecule; specific examples include Dnp, and so on.

In one embodiment, peptides that serve as substrates for deacetylases can include a peptide with an amino terminal Boc group, amino acid residues, an acetylated lysine residue, and an MCA group, C terminal to the lysine (e.g., adjacent). Boc represents a protecting group for the amino group at the N-terminal position of the peptide. MCA is a fluorescent substance; and the epsilon-amino group of the flanking lysine residue is acetylated. When the peptides is cleaved at the carboxyl-terminal side of the lysine residue, they release AMC. Since the emission wavelength of the released AMC differs from that of peptidyl-MCA, the quantity of cleaved substrates can be determined using the fluorescence intensity of AMC as an index.

The following assays provide methods (also referred to herein as "evaluating a compound" or "screening a compound") for identifying modulators, i.e., candidate or test compounds (e.g., peptides, peptidomimetics, small molecules or other drugs) which interact with and/or modulate, e.g., have a stimulatory or inhibitory effect on, for example, cytochrome c acetylation status. Such compounds can be agonists or antagonists of deacetylation, e.g., agonist or antagonist of a SIR polypeptide. In preferred embodiments, the screening assays described herein are used to identify candidates which function as deacetylation antagonists. As described herein, such antagonists can decrease apoptosis of a cell, which has practical utility, e.g., in altering life span regulation. In other preferred embodiment, the screening assays described herein are used to identify candidates which function as deacetylation agonists. As described herein, such agonists can increase apoptosis of a cell, which has practical utility, e.g., in cancer. Some of these assays may be performed in animals, e.g., mammals, in organs, in cells. Others may be performed in animals, e.g., mammals, in organs, in cells, in cell extracts, e.g., purified or unpurified nuclear extracts, intracellular extracts, in purified preparations, in cell-free systems, in cell fractions enriched for certain components, e.g., organelles or compounds, or in other systems known in the art. Given the teachings herein and the state of the art, a person of ordinary skill in the art would be able to choose an appropriate system and assay for practicing the methods of the present invention.

Some exemplary screening assays for assessing activity or function include one or more of the following features:

use of a transgenic cell, e.g., with a transgene encoding a polypeptide having acetylation or deacetylation activity and/or a cytochrome c polypeptide or mutants thereof;

use of a mammalian cell that expresses a polypeptide having acetylation or deacetylation activity and/or cytochrome c;

detection of binding of a labeled compound to a polypeptide having acetylation or deacetylation activity or cytochrome c where the compound is, for example, a peptide, protein, antibody or small organic molecule; e.g., the compound interferes with or disrupts an interaction between the polypeptide and cytochrome c;

use of proximity assays that detect interaction between a polypeptide having acetylation or deacetylation activity and a substrate, e.g., cytochrome c, or fragments thereof, for example, fluorescence proximity assays.

use of a two hybrid assay to detect interaction between a polypeptide having acetylation or deacetylation activity and cytochrome c or fragments thereof. In some instances, the two hybrid assay can be evaluated in the presence of a test compound, e.g., to determine if the test compound disrupts or interferes with an interaction. Two hybrid assays can, for example, be conducted using yeast or bacterial systems.

use of radio-labeled substrates, e.g. $^{35}S$, $^{3}H$, $^{14}C$, e.g., to determine acetylation status, metabolic status, rate of protein synthesis, inter alia.

use of antibodies specific for certain acetylated or de-acetylated forms of the substrate.

Various screening assays are described in more detail below.

Any assay herein, e.g., an in vitro assay or an in vivo assay, can be performed individually, e.g., just with the test compound, or with appropriate controls. For example, a parallel assay without the test compound, or other parallel assays without other reaction components, e.g., without a target or without a substrate. Alternatively, it is possible to compare assay results to a reference, e.g., a reference value, e.g., obtained from the literature, a prior assay, and so forth. Appropriate correlations and art known statistical methods can be used to evaluate an assay result.

A "compound" or "test compound" can be any chemical compound, for example, a macromolecule (e.g., a polypeptide, a protein complex, or a nucleic acid) or a small molecule (e.g., an amino acid, a nucleotide, an organic or inorganic compound). The test compound can have a formula weight of less than about 10,000 grams per mole, less than 5,000 grams per mole, less than 1,000 grams per mole, or less than about 500 grams per mole. The test compound can be naturally occurring (e.g., a herb or a nature product), synthetic, or both. Examples of macromolecules are proteins, protein complexes, and glycoproteins, nucleic acids, e.g., DNA, RNA and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds. A test compound can be the only substance assayed by the method described herein. Alternatively, a collection of test compounds can be assayed either consecutively or concurrently by the methods described herein.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat.*

*Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., *Science,* 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckemmann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., framework).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

The test compounds of the present invention can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological libraries include libraries of nucleic acids and libraries of proteins. Some nucleic acid libraries encode a diverse set of proteins (e.g., natural and artificial proteins; others provide, for example, functional RNA and DNA molecules such as nucleic acid aptamers or ribozymes. A peptoid library can be made to include structures similar to a peptide library. (See also Lam (1997) *Anticancer Drug Des.* 12:145). A library of proteins may be produced by an expression library or a display library (e.g., a phage display library).

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

In Vitro Assays

In some embodiments, interaction with, e.g., binding of, a polypeptide having acetylation or deacetylation activity, can be assayed in vitro. The reaction mixture can include a co-factor of the polypeptide such as NAD and/or a NAD analog.

In other embodiments, the reaction mixture can include a cytochrome c, and compounds can be screened, e.g., in an in vitro assay, to evaluate the ability of a test compound to modulate interaction between the polypeptide and a substrate, e.g., a cytochrome c. This type of assay can be accomplished, for example, by coupling one of the components, with a radioisotope or enzymatic label such that binding of the labeled component to the other can be determined by detecting the labeled compound in a complex. A component can be labeled with $^{125}$I, $^{35}$S, $^{14}$C, or $^{3}$H, either directly or indirectly, and the radioisotope detected by direct counting of radioemmission or by scintillation counting. Alternatively, a component can be enzymatically labeled with, for example, horseradish peroxidase, alkaline phosphatase, or luciferase, and the enzymatic label detected by determination of conversion of an appropriate substrate to product. Competition assays can also be used to evaluate a physical interaction between a test compound and a target.

Cell-free assays involve preparing a reaction mixture of the target protein (e.g., a SIR polypeptide) and the test compound under conditions and for a time sufficient to allow the two components to interact and bind, thus forming a complex that can be removed and/or detected.

The interaction between two molecules can also be detected, e.g., using a fluorescence assay in which at least one molecule is fluorescently labeled. One example of such an assay includes fluorescence energy transfer (FET or FRET for fluorescence resonance energy transfer) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A FET binding event can be conveniently measured through standard fluorometric detection means well known in the art (e.g., using a fluorimeter).

Another example of a fluorescence assay is fluorescence polarization (FP). For FP, only one component needs to be labeled. A binding interaction is detected by a change in molecular size of the labeled component. The size change alters the tumbling rate of the component in solution and is detected as a change in FP. See, e.g., Nasir et al. (1999) *Comb Chem HTS* 2:177-190; Jameson et al. (1995) *Methods Enzymol* 246:283; Seethala et al. (1998) *Anal Biochem.* 255:257.

Fluorescence polarization can be monitored in multiwell plates, e.g., using the Tecan Polarion™ reader. See, e.g., Parker et al. (2000) *Journal of Biomolecular Screening* 5:77-88; and Shoeman, et al. (1999) 38, 16802-16809.

In another embodiment, determining the ability of the protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, a polypeptide, e.g., a SIR polypeptide, is anchored onto a solid phase. The polypeptide/test compound complexes anchored on the solid phase can be detected at the end of the reaction, e.g., the binding reaction. For example, a SIR polypeptide can be anchored onto a solid surface, and the test compound, (which is not anchored), can be labeled, either directly or indirectly, with detectable labels discussed herein.

It may be desirable to immobilize either the polypeptide or an antibody to the polypeptide to facilitate separation of complexed from uncomplexed forms of one or both of the proteins, as well as to accommodate automation of the assay. Binding of a test compound to a polypeptide, or interaction of a protein with a second component in the presence and absence of a candidate compound, can be accomplished in any vessel suitable for containing the reactants. Examples of such vessels include microtiter plates, test tubes, and microcentrifuge tubes. In one embodiment, a fusion protein can be provided which adds a domain that allows one or both of the proteins to be bound to a matrix. For example, glutathione-S-transferase/SIR polypeptide fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or a SIR protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of polypeptide binding or activity determined using standard techniques.

Other techniques for immobilizing either a protein or a target molecule on matrices include using conjugation of biotin and streptavidin. Biotinylated protein or target molecules can be prepared from biotin-NHS(N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed: Where the previously non-immobilized component is not pre-labeled, an indirect label can be used to detect complexes anchored on the surface, e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with a protein or target molecules but which do not interfere with binding of the protein to its target molecule. Such antibodies can be derivatized to the wells of the plate, and unbound target or the protein trapped in the wells by antibody conjugation. Methods for detecting such complexes, in addition to those described above for the GST-immobilized complexes, include immunodetection of complexes using antibodies reactive with the protein or target molecule, as well as enzyme-linked assays which rely on detecting an enzymatic activity associated with the protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., (1993) *Trends Biochem Sci* 18:284-7); chromatography (gel filtration chromatography, ion-exchange chromatography); electrophoresis (see, e.g., Ausubel, F. et al., eds. Current Protocols in Molecular Biology 1999, J. Wiley: New York.); and immunoprecipitation (see, for example, Ausubel, F. et al., eds. (1999) *Current Protocols in Molecular Biology*, J. Wiley: New York). Such resins and chromatographic techniques are known to one skilled in the art (see, e.g., Heegaard, N. H., (1998) *J Mol Recognit* 11:141-8; Hage, D. S., and Tweed, S. A. (1997) *J Chromatogr B Biomed Sci Appl.* 699:499-525). Further, fluorescence energy transfer may also be conveniently utilized, as described herein, to detect binding without further purification of the complex from solution.

In a preferred embodiment, the assay includes contacting the protein or biologically active portion thereof with a known compound which binds a protein to form an assay mixture, contacting the assay mixture with a test compound, and determining the ability of the test compound to interact with a protein, wherein determining the ability of the test compound to interact with the protein includes determining the ability of the test compound to preferentially bind to the protein or biologically active portion thereof, or to modulate the activity of a target molecule such as acetylation status, as compared to the known compound.

The target products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target product. Such compounds can include, but are not limited to molecules such as antibodies, peptides, and small molecules.

To identify compounds that interfere with the interaction between the target product and its binding partner(s), a reaction mixture containing the target product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target and its cellular or extracellular binding partner. Control reaction mixtures are incubated without the test compound or with a placebo. The formation of any complexes between the target product and the cellular or extracellular binding partner is then detected. The formation of a complex in the control reaction, but not in the reaction mixture containing the test compound, indicates that the compound interferes with the interaction of the target product and the interactive binding partner. Additionally, complex formation within reaction mixtures containing the test compound and normal target product can also be compared to complex formation within reaction mixtures containing the test compound and mutant target product. This comparison can be important in those cases wherein it is desirable to identify compounds that disrupt interactions of mutant but not normal target products.

These assays can be conducted in a heterogeneous or homogeneous format. Heterogeneous assays involve anchoring either the target product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target product or the partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target product and the interactive cellular or extracellular binding partner product is prepared in that either the target products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target product-binding partner interaction can be identified.

Many of the screening assays described herein have discussed screening for molecules with regard to a SIR protein or other protein having acetylation or deacetylation activity, however, the same assays can also be used to screen for molecules with regard to cytochrome c.

In yet another aspect, the polypeptide can be used as "bait proteins" in a two-hybrid assay or three-hybrid assay (see, e.g., U.S. Pat. No. 5,283,317; Zervos et al. (1993) *Cell* 72:223-232; Madura et al. (1993) *J. Biol. Chem.* 268:12046-12054; Bartel et al. (1993) *Biotechniques* 14:920-924; Iwabuchi et al. (1993) *Oncogene* 8:1693-1696; and Brent WO94/10300), to identify other proteins, which bind to or interact with a polypeptide ("polypeptide binding partners") and are involved in acetylation status of cytochrome c. Such a polypeptide binding partner can be an activator or inhibitor of signals by the proteins.

The two-hybrid system is based on the modular nature of most transcription factors, which consist of separable DNA-binding and activation domains. Briefly, the assay utilizes two different DNA constructs. In one construct, the gene that codes for a protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the protein can be the fused to the activator domain.) If the "bait" and the "prey" proteins are able to interact, in vivo, forming a polypeptide-dependent complex, the DNA-binding and activation domains of the transcription factor are brought into close proximity. This proximity allows transcription of a reporter gene (e.g., lacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protein, e.g., the protein having acetylation or deacetylation activity. In another embodiment, the two-hybrid assay is used to monitor an interaction between two components, e.g., a polypeptide having acetylation or deacetylation activity such as a SIR polypeptide and, e.g., cytochrome c, that are known to interact. The two hybrid assay is conducted in the presence of a test compound, and the assay is used to determine whether the test compound enhances or diminishes the interaction between the components.

In another embodiment, modulators of gene expression are identified. For example, a cell or cell free mixture is contacted with a candidate compound and the expression of the mRNA or protein evaluated relative to the level of expression of mRNA or protein in the absence of the candidate compound. When expression of the mRNA or protein is greater in the presence of the candidate compound than in its absence, the candidate compound is identified as a stimulator of mRNA or protein expression. Alternatively, when expression of the mRNA or protein is less (statistically significantly less) in the presence of the candidate compound than in its absence, the candidate compound is identified as an inhibitor of the mRNA or protein expression. The level of the mRNA or protein expression can be determined by methods for detecting mRNA or proteins, e.g., using probes or antibodies, e.g., labeled probes or antibodies.

Cell-Based Assays

In another embodiment, the assay, e.g., the assay for selecting compounds which interact with a polypeptide and/or which effect (e.g., induce) apoptosis, can be a cell-based assay. The cell based assay can include contacting a cell expressing a polypeptide having acetylation or deacetylation activity and/or cytochrome c with a test compound and determining the ability of the test compound to modulate (e.g. stimulate or inhibit) an activity of the polypeptide or cytochrome c, and/or determine the ability of the test compound to modulate polypeptide and/or cytochrome c expression, e.g., by detecting nucleic acids (e.g., mRNA or cDNA) or proteins in the cell. A preferred activity is the deacetylation function of a polypeptide of cytochrome c; a further preferred activity is the ability to cause apoptosis. Determining the ability of the test compound to modulate the activity of a polypeptide can be accomplished, for example, by determining the ability of a polypeptide to bind to or interact with the test molecule, and by determining the ability of the test molecule to stimulate apoptosis. Cell-based systems can be used to identify compounds that decrease the polypeptides expression and/or activity and/or effect, e.g., decrease or prevent apoptosis, or visa versa. Such cells can be recombinant or non-recombinant, such as cell lines that express the gene encoding the polypeptide and/or the cytochrome c gene. In some embodiments, the cells can be recombinant or non-recombinant cells which express a transcription factor. Preferred systems are mammalian or yeast cells that express a polypeptide having acetylation or deacetylation activity and cytochrome c. In utilizing such systems, cells are exposed to compounds suspected of decreasing expression of a deacetylating polypeptide and/or decreasing deacetylation activity of the polypeptide and/or reducing apoptosis, or compounds suspected of increasing expression of a deacetylating polypeptide and/or increasing a deacetylation activity and/or inducing apoptosis. After exposure, the cells are assayed, for example, for expression of the gene or activity of the protein. Alternatively, the cells may also be assayed for the inhibition of the deacetylation function of a polypeptide, or the apoptotic or cytostatic function. In one embodiment, the visual assessment can be used for evidence of apoptosis, e.g., nuclear fragmentation.

Another preferred cell for a cell-based assay comprises a yeast cell transformed with a vector comprising the Sir2 gene, a homolog of human a SIRT1. One use for a yeast cell expressing Sir2 is to mutagenize the yeast and screen for yeast that will survive only when the Sir2 polypeptide is functioning normally. Synthetic lethal screens are described in Holtzman et al. (1993), *J. Cell Bio.* 122: 635-644. The yeast that require Sir2 function for survival can then be used to screen test compounds for those that inhibit Sir2 activity. Test compounds that results in a decrease in yeast survival are likely inhibitors of Sir2 in this system.

A cell used in the methods of the invention can be from a stable cell line or a primary culture obtained from an organism, e.g., a organism treated with the test compound.

In addition to cell-based and in vitro assay systems, non-human organisms, e.g., transgenic non-human organisms, can also be used. A transgenic organism is one in which a heterologous DNA sequence is chromosomally integrated into the germ cells of the animal. A transgenic organism will also have the transgene integrated into the chromosomes of its somatic cells. Organisms of any species, including, but not limited to: yeast, worms, flies, fish, reptiles, birds, mammals (e.g., mice, rats, rabbits, guinea pigs, pigs, micro-pigs, and goats), and non-human primates (e.g., baboons, monkeys, chimpanzees) may be used in the methods of the invention.

A transgenic cell or animal used in the methods of the invention can include a transgene that encodes, e.g., a copy of a polypeptide having acetylation or deacetylation activity and/or cytochrome c, e.g., a polypeptide having acetylation or deacetylation activity or cytochrome c polypeptide that was evaluated for an interaction with the test compound. The transgene can encode a protein that is normally exogenous to the transgenic cell or animal, including a human protein, e.g., a human SIR polypeptide and/or human cytochrome c. The transgene can be linked to a heterologous or a native promoter. Methods of making transgenic cells and animals are known in the art.

Accordingly, in another embodiment, the invention features a method of identifying a compound as a candidate of treatment of unwanted cell proliferation, e.g., cancer treatment. The method includes: providing a compound which interacts with, e.g., binds to, a SIR polypeptide; evaluating the effect of the compound on apoptosis, wherein a compound that results in apoptosis is subjected to further evaluation steps; and further evaluating the effect of the test compound on a subject, e.g., an animal model, e.g., an animal model for cancer.

The interaction between a test compound and the polypeptide having acetylation or deacetylation activity, e.g., a SIR polypeptide, can be performed by any of the methods described herein, e.g., using cell-based assays or cell-free in vitro assays.

Cytochrome c can be detected using a monoclonal antibody (clone 7H 8.2C12, PharMingen, San Diego, Calif.), Structural Activity Relationships It is also possible to use structure-activity relationships (SAR) and structure-based design principles to find compounds that have improved effects on a polypeptide having acetylation or deacetylation activity. SARs provide information about the activity of related compounds in at least one relevant assay. Correlations are made between structural features of a compound of interest and an activity. For example, it may be possible by evaluating SARs for a family of compounds that interact with a polypeptide to identify one or more structural features required for activity. A library of compounds can then be produced that vary these features, and then the library is screened. Structure-based design can include determining a structural model of the physical interaction of the compound and its target. The structural model can indicate how an antagonist of the target can be engineered. Such antagonist may be useful in altering lifespan regulation.

Both the SAR and the structure-based design approach can be used to identify a pharmacophore. Pharmacophores are a highly valuable and useful concept in drug discovery and drug-lead optimization. A pharmacophore is defined as a distinct three dimensional (3D) arrangement of chemical groups essential for biological activity. Since a pharmaceutically active molecule must interact with one or more molecular structures within the body of the subject in order to be effective, and the desired functional properties of the molecule are derived from these interactions, each active compound must contain a distinct arrangement of chemical groups which enable this interaction to occur. The chemical groups, commonly termed descriptor centers, can be represented by (a) an atom or group of atoms; (b) pseudo-atoms, for example a center of a ring, or the center of mass of a molecule; (c) vectors, for example atomic pairs, electron lone pair directions, or the normal to a plane. Once formulated a pharmacophore can be used to search a database of chemical compound, e.g., for those having a structure compatible with the pharmacophore. See, for example, U.S. Pat. No. 6,343,257; Y. C. Martin, 3D Database Searching in Drug Design, J. Med. Chem. 35, 2145(1992); and A. C. Good and J. S. Mason, Three Dimensional Structure Database Searches, Reviews in Comp. Chem. 7, 67(1996). Database search queries are based not only on chemical property information but also on precise geometric information.

Computer-based approaches can use database searching to find matching templates; Y. C. Martin, Database searching in drug design, J. Medicinal Chemistry, vol. 35, pp 2145-54 (1992), which is herein incorporated by reference. Existing methods for searching 2-D and 3-D databases of compounds are applicable. Lederle of American Cyanamid (Pearl River, N.Y.) has pioneered molecular shape-searching, 3D searching and trend-vectors of databases. Commercial vendors and other research groups also provide searching capabilities (MACSS-3D, Molecular Design Ltd. (San Leandro, Calif.); CAVEAT, Lauri, G et al., University of California (Berkeley, Calif.); CHEM-X, Chemical Design, Inc. (Mahwah, N.J.)). Software for these searches can be used to analyze databases of potential drug compounds indexed by their significant chemical and geometric structure (e.g., the Standard Drugs File (Derwent Publications Ltd., London, England), the Bielstein database (Bielstein Information, Frankfurt, Germany or Chicago), and the Chemical Registry database (CAS, Columbus, Ohio)).

Once a compound is identified that matches the pharmocophore, it can be tested for activity, e.g., for binding to a component of a polypeptide and/or for a biological activity, e.g., deacetylation and/or apoptosis. See, e.g., the Screening Methods described above.

Organismal Assays

Still other methods for evaluating a test compound include organismal based assays, e.g., using a mammal (e.g., a mouse, rat, primate, or other non-human), or other animal (e.g., *Xenopus*, zebrafish, or an invertebrate such as a fly or nematode). In some cases, the organism is a transgenic organism, e.g., an organism which includes a heterologous SIR and/or cytochrome c component, (e.g., from a mammal, e.g., a human). The test compound can be administered to the organism once or as a regimen (regular or irregular). A parameter of the organism is then evaluated, e.g., an age-associated parameter or a parameter of the cytochrome c-mediated apoptosis pathway. Test compounds that are indicated as of interest result in a change in the parameter relative to a reference, e.g., a parameter of a control organism. Other parameters (e.g., related to toxicity, clearance, and pharmacokinetics) can also be evaluated.

In some embodiment, the test compound is evaluated using an animal that has a particular disorder, e.g., an age associated disorder. These disorders provide a sensitized system in which the test compound's effects on physiology can be observed. Exemplary disorders include: denervation, disuse atrophy; metabolic disorders (e.g., disorder of obese and/or diabetic animals such as db/db mouse and ob/ob mouse); cerebral, liver ischemia; cisplatin/taxol/vincristine models; various tissue (xenograph) transplants; transgenic bone models; Pain syndromes (include inflammatory and neuropathic disorders); Paraquot, genotoxic, oxidative stress models; pulmonary obstruction (e.g., asthma models); and tumor models. In a preferred embodiment, the animal model is an animal that has an altered phenotype when calorically restricted. For example, F344 rats provide a useful assay system for evaluating a test compound. When calorically restricted, F344 rats have a 0 to 10% incidence of nephropathy. However, when fed ad libitum, they have a 60 to 100% incidence of nephropathy. See Table 2.

TABLE 2

F344 rats - Frequency of nephropathy.

| Months | Ad lib | CR |
|---|---|---|
| 6 | 0% | 0% |
| 12 | 60% | 0% |
| 18 | 100% | 0% |
| 24 | 100% | 0% |

Additional animals are listed in Table 2:

TABLE 3

| Model | Mean Lifespan (months) Ad lib | CR | Predisposition |
|---|---|---|---|
| SH Rat | 18 | 30 | Hypertension |
| SA Mouse | 10 | 15 | Amyloid |
| NZB Mouse | 12 | 16 | SLE |
| kd/kd Mouse | 8 | 18 | Nephritis |
| MRL/1 Mouse | 6 | >15 | Autoimmune |
| ob/ob Mouse | 14 | 26 | Diabetes |

To evaluate a test compound, it is administered to the animal (e.g., an F344 rat or an animal listed in Table 3), and a parameter of the animal is evaluated, e.g., after a period of time. The animal can be fed ad libitum or normally (e.g., not under caloric restriction, although some parameters can be evaluated under such conditions). Typically, a cohort of such animals is used for the assay. Generally, a test compound can be indicated as favorably altering lifespan regulation in the animal if the test compound affects the parameter in the direction of the phenotype of a similar animal subject to caloric restriction. Such test compounds may cause at least some of the lifespan regulatory effects of caloric restriction, e.g., a subset of such effects, without having to deprive the organism of caloric intake.

In one embodiment, the parameter is an age-associated or disease associated parameter, e.g., a symptom of the disorder associated with the animal model (e.g., the disorder in the "Predisposition column of Table 3). For example, the test compound can be administered to the SH Rat, and blood pressure is monitored. A test compound that is favorably indicated can cause an amelioration of the symptom relative to a similar reference animal not treated with the compound.

Still other in vivo models and organismal assays include:
insulin sensitivity;
Tumors: spontaneous, induced, grafts, cytochrome c−, cytochrome c+;
Autoimmune: NZB mice;
Cognition: learning & memory models;
Bone disease: ovariectomy osteoporosis model;
Joint disease: adjuvant arthritis;
Kidney disease: kd/kd mice;
Diabetes & complications: streptozotocin model; and
Canine stroke & ischemia models.

In assessing whether a test compound is capable of inhibiting the cytochrome c-mediated apoptosis pathway for the purpose of altering life span regulation, a number of age-associated parameters or biomarkers can be monitored or evaluated. Exemplary age associated parameters include: (i)

lifespan of the cell or the organism; (ii) presence or abundance of a gene transcript or gene product in the cell or organism that has a biological age-dependent expression pattern; (iii) resistance of the cell or organism to stress; (iv) one or more metabolic parameters of the cell or organism; (v) proliferative capacity of the cell or a set of cells present in the organism; and (vi) physical appearance or behavior of the cell or organism.

Characterization of molecular differences between two such organisms, e.g., one reference organism and one organism treated with an cytochrome c-mediated apoptosis modulator can reveal a difference in the physiological state of the organisms. The reference organism and the treated organism are typically the same chronological age. Generally, organisms of the same chronological age may have lived for an amount of time within 15, 10, 5, 3, 2 or 1% of the average lifespan of a wild type organism of that species. In a preferred embodiment, the organisms are adult organisms, e.g. the organisms have lived for at least an amount of time in which the average wild type organism has matured to an age at which it is competent to reproduce.

In some embodiments, the organismal screening assay is performed before the organisms exhibit overt physical features of aging. For example, the organisms may be adults that have lived only 10, 30, 40, 50, 60, or 70% of the average lifespan of a wild type organism of the same species.

Age-associated changes in metabolism, immune competence, and chromosomal structure have been reported. Any of these changes can be evaluated, either in a test subject (e.g., for an organism based assay), or for a patient (e.g., prior, during or after treatment with a therapeutic described herein.

In another embodiment, a marker associated with caloric restriction is evaluated in a subject organism of a screening assay (or a treated subject). Although these markers may not be age-associated, they may be indicative of a physiological state that is altered when the cytochrome c-mediated apoptosis pathway is modulated. The marker can be an mRNA or protein whose abundance changes in calorically restricted animals. WO 01/12851 and U.S. Pat. No. 6,406,853 describe exemplary markers.

In a related aspect, the invention features a method of evaluating a test compound using a plurality of biomarkers. This can be done by profiling the sample. The method includes providing a cell or organism and a test compound; contacting the test compound to the cell; obtaining a subject expression profile for the contacted cell; and comparing the subject expression profile to one or more reference profiles. The profiles include a value representing the level of expression of molecules previously determined to be correlated with SIR activity and/or the cytochrome c-mediated apoptosis (see, e.g., below). In a preferred embodiment, the subject expression profile is compared to a target profile, e.g., a profile for a normal cell or for desired condition of a cell. The test compound is evaluated favorably if the subject expression profile is more similar to the target profile than an expression profile obtained from an uncontacted cell.

Similarity of profiles can be determined by a variety of metric, including Euclidean distance in a n-dimensional space, where n is the number of different values within the profile. Other metrics, for example, include weighting factors that basis different values according to their importance for the comparison.

Profiles, e.g., profiles obtained from nucleic acid array or protein arrays can be used to compare samples and/or cells in a variety of states as described in Golub et al. ((1999) *Science* 286:531). In one embodiment, multiple expression profiles from different conditions and including replicates or like samples from similar conditions are compared to identify nucleic acids whose expression level is predictive of the sample and/or condition. Each candidate nucleic acid can be given a weighted "voting" factor dependent on the degree of correlation of the nucleic acid's expression and the sample identity. A correlation can be measured using a Euclidean distance or the Pearson correlation coefficient.

Combinatorial Systems

The organisms described herein may be deficient in the activity of any protein that is associated with aging, e.g., associated with the regulation of lifespan. Some exemplary genes and homologs of genes which encode proteins that are associated with the regulation of lifespan are listed in Table 1. For example, mutant or otherwise altered (e.g., RNAi treated or transgenic) organisms that are altered for SIR activity or a cytochrome c-apoptosis activity can also include an alteration in a component that is listed in Table 1 or that directly interacts with a component in Table 1.

Other types of combinatorial systems include environmental treatment of an organism that is mutant or otherwise altered (e.g., RNAi treated or transgenic) with respect to SIR polypeptide activity and/or cytochrome c-mediated apoptotic activity. Exemplary environmental treatments include stress (e.g., oxidative stress, genotoxic stress, $H_2O_2$, heavy metal exposure), caloric restriction, and treatment with a drug, e.g., a histone deacetylase inhibitor.

TABLE 1

| Organism | Gene name | Description | Exemplary homologs |
|---|---|---|---|
| S. cerevisiae | SIR2 | NAD-dependent histone deacetylase | Murine Sir2alpha (GenBank AccNo: AF214646), human A SIR POLYPEPTIDE (GenBank Acc No: AF083106) human Sir2 SIRT3 GenBank Accession No: AF083108; human Sir2 SIRT4 GenBank Accession No: AF083109; human Sir2 SIRT5 GenBank Accession No: AF083110 |
| | SIR3 | Regulator of chromatin silencing | |
| | SIR4 | Regulator of chromatin silencing | |
| | RPD3 | Histone deacetylase | |
| | FOB1 | Suppresses rDNA replication | |
| | SGS1 | Werners-like DNA helicase | |
| | SNF1 | Kinase involved in carbon source utilization | |
| | SIP2 | SNF1 co-repressor | |
| | SNF4 | SNF1 co-activator | |
| | NPT1 | Involved in NAD synthesis | |
| | RTG2 | Sensor of mitochondrial disfunction | |
| | Coq7 | Regulator of ubiquinone synthesis | |

TABLE 1-continued

| Organism | Gene name | Description | Exemplary homologs |
|---|---|---|---|
| C. elegans | Daf-2 | Insulin/IGF-1 receptor homolog | insulin or IGF receptor |
| | Age-1 | PI(3) kinase | PI(3) kinase |
| | Pdk-1 | | PDK-1 |
| | Daf-18 | Phosphatase | PTEN |
| | Daf-16 | Forkhead/winged-helix family transcription factor | AFX, FKHR, FKHRL1 |
| | Ceinsulin-1 | Insulin/IGF-1-like homolog | insulin or IGF molecules |
| | Ctl-1 | Cytosolic catalase | |
| | MEV-1 | Cytochrome B subunit of mitochondrial succinate dehydrogenase | Cytochrome B subunit of mitochondrial succinate dehydrogenase |
| | Sod-3 | Mn-superoxide dismutase | superoxide dismutase |
| | Clk-1 | Regulator of ubiquinone synthesis | |
| | [Eat mutants] | | |
| | Tkr-1 | Tyrosine kinase | |
| | Spe-10 | Unknown (sperm defective) | |
| | Spe-26 | Unknown (sperm defective) | |
| | Old-1 | Receptor tyrosine kinase | |
| | Kin-29 | Serine Threonine Kinase | |
| Drosophila | Indy GenBank accession no. AE003519 | Carboxylate transporter | hNaDC-1, accession No. U26209, SDCT2, accession no. AF081825, NaDC-1, accession no. U12186, mNaDC-1, accession no. AF 201903, human solute carrier family 13, member 2 GenBank NP_003975.1, human sodium-dependent high-affinity dicarboxylate transporter 3, human carrier family 13 (sodium/sulfate symporters), member 1, human hypothetical protein XP_091606, human carrier family 13 (sodium/sulfate symporters) member 4 (GenBank NP_036582), |
| | Cu/Zn-SOD | superoxide dismutase | |
| | Methuselah | Putative G-protein-coupled 7 transmembrane domain receptor | |
| Mus musculus | p66shc | Signaling adaptor | |
| | PROP1 | Homeodomain protein | |
| | Growth hormone | | |
| | Growth hormone Releasing hormone receptor | | |

RNAi

It is also possible to regulate activity of a polypeptide having acetylation or deacetylation activity and/or cytochrome c-mediated apoptotic activity using a double-stranded RNA (dsRNA) that mediates RNA interference (RNAi). The dsRNA can be delivered to cells or to an organism. Endogenous components of the cell or organism can trigger RNA interference (RNAi) which silences expression of genes that include the target sequence. dsRNA can be produced by transcribing a cassette in both directions, for example, by including a T7 promoter on either side of the cassette. The insert in the cassette is selected so that it includes a sequence complementary to a nucleic acid encoding a component of the cytochrome c-mediate apoptosis pathway. The sequence need not be full length, for example, an exon, or at least 50 nucleotides. The sequence can be from the 5' half of the transcript, e.g., within 1000, 600, 400, or 300 nucleotides of the ATG See also, the HiScribe™ RNAi Transcription Kit (New England Biolabs, MA) and Fire, A. (1999) Trends Genet. 15, 358-363.

dsRNA can be digested into smaller fragments. See, e.g., US Patent Application 2002-0086356 and 2003-0084471. In one embodiment, an siRNA is used. siRNAs are small double stranded RNAs (dsRNAs) that optionally include overhangs. For example, the duplex region is about 18 to 25 nucleotides in length, e.g., about 19, 20, 21, 22, 23, or 24 nucleotides in length. Typically the siRNA sequences are exactly complementary to the target mRNA.

dsRNAs (and siRNA's in particular) can be used to silence gene expression in mammalian cells. See, e.g., Clemens, J. C. et al. (2000) Proc. Natl. Sci. USA 97, 6499-6503; Billy, E. et al. (2001) Proc. Natl. Sci. USA 98, 14428-14433; Elbashir et al. (2001) *Nature*. 411(6836):494-8; Yang, D. et al. (2002) Proc. Natl. Acad. Sci. USA 99, 9942-9947.

dsRNA molecules can be used to provide cells and organisms (e.g., mammalian cells and organisms, and nematode mammalian cells and organisms) that are deficient in a deacetylation, acetylation, and/or cytochrome c-mediated apoptotic activity. Such cells and organisms are useful tools for evaluating heterologous molecules and test compounds for activity, e.g., an activity that modulates lifespan regulation.

Pharmaceutical Compositions

A compound that modulates the cytochrome c-mediated apoptotic pathway, e.g., modulates expression and/or activity of a polypeptide having acetylation or deacetylation activity and/or cytochrome c can be incorporated into a pharmaceutical composition for administration to a subject, e.g., a human, a non-human animal, e.g., an animal patient (e.g., pet or agricultural animal) or an animal model (e.g., an animal model for aging or a metabolic disorder (e.g., a pancreatic or insulin related disorder). Such compositions typically include a small molecule (e.g., a small molecule that is a SIR activator, or a SIR inactivator), nucleic acid molecule, protein, or antibody and a pharmaceutically acceptable carrier. As used herein the language "pharmaceutically acceptable carrier"

includes solvents, dispersion media, coatings, antibacterial and antifungal agents, isotonic and absorption delaying agents, and the like, compatible with pharmaceutical administration. Other active compounds can also be incorporated into the compositions.

Exemplary compounds that can be used for inducing acetylation of cytochrome c and/or decreasing apoptosis can include antisense to a deacetylating polypeptide, RNAi, an antibody, an intrabody, and other compounds identified by a method described herein, e.g., compounds that reduce apoptosis in a deacetylating polypeptide and cytochrome c expressing cell. Exemplary compounds that can be used for reducing acetylation of cytochrome c and/or increasing apoptosis can include a purified deacetylating polypeptide, expression of a deacetylating polypeptide from heterologous genes, or by increasing the expression of endogenous sequence encoding a deacetylating polypeptide and other compounds identified by a method described herein, e.g., compounds that induces apoptosis in a deacetylating polypeptide and cytochrome c expressing cell.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells, e.g., a pituitary cell) can also be used as pharmaceutically acceptable carriers. These can be prepared according to methods known to those skilled in the art, for example, as described in U.S. Pat. No. 4,522, 811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments.

For antibody compounds that modulate SIR components, one preferred dosage is 0.1 mg/kg of body weight (generally 10 mg/kg to 20 mg/kg). Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration. A method for lipidation of antibodies is described by Cruikshank et al. ((1997) *J. Acquired Immune Deficiency Syndromes and Human Retrovirology* 14:193).

The present invention encompasses agents that modulate acetylation status of cytochrome c and the cytochrome c-mediated apoptotic pathway. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The nucleic acid molecules that modulate expression of a polypeptide having acetylation or deacetylation activity and or activity the polypeptide and/or the cytochrome c-mediated apoptotic pathway can be inserted into vectors and used as gene therapy vectors. For example, the nucleic acid can encode a SIR polypeptide. Gene therapy vectors can be delivered to a subject by, for example, intravenous injection, local administration (see U.S. Pat. No. 5,328,470) or by stereotactic injection (see e.g., Chen et al. *Proc. Natl. Acad. Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Further, a variety of techniques may be utilized to modulate (e.g., increase or inhibit) the expression, synthesis, or activity of target genes and/or proteins. Such molecules may include, but are not limited to small organic molecules, peptides, purified polypeptide, sequences encoding the polypeptides, or molecules which increase the expression of endogenous sequence encoding the polypeptide, or other deacetylation agonists described herein.

Modulating Lifespan Regulation in Subjects

Agents that alter acetylation status of cytochrome c and the cytochrome c-mediated apoptotic activity can be used to modulate lifespan regulation in subjects, e.g., animal (e.g., mammalian, e.g., human subjects). The compositions can be administered to a subject, e.g., an adult subject, e.g., a healthy adult subject or a subject having an age-related disease. In the latter case, the method can include evaluating a subject, e.g., to characterize a symptom of an age-related disease or other disease marker, and thereby identifying a subject as having an age-related disease or being pre-disposed to such a disease. Exemplary age-related diseases include: cancer (e.g., breast cancer, colorectal cancer, CCL, CML, prostate cancer); skeletal muscle atrophy; adult-onset diabetes; diabetic nephropathy, neuropathy (e.g., sensory neuropathy, autonomic neuropathy, motor neuropathy, retinopathy); obesity; bone resorption; age-related macular degeneration, AIDS related dementia, ALS, Alzheimer's, Bell's Palsy, atherosclerosis, cardiac diseases (e.g., cardiac dysrhythmias, chronic congestive heart failure, ischemic stroke, coronary artery disease and cardiomyopathy), chronic renal failure, type 2 diabetes, ulceration, cataract, presbiopia, glomerulonephritis, Guillan-Barre syndrome, hemorrhagic stroke, rheumatoid arthritis, inflammatory bowel disease, multiple sclerosis, SLE, Crohn's disease, osteoarthritis, Parkinson's disease, pneumonia, Touret's syndrome, and urinary incontinence. Symptoms and diagnosis of such diseases are well known to medical practitioners. The compositions may also be administered to individuals being treated by other means for such diseases, for example, individuals being treated with a chemotherapeutic (e.g., and having neutropenia, atrophy, cachexia, nephropathy, neuropathy) or an elective surgery.

Subjects can be diagnosed and evaluated, e.g., before, during, and after treatment. Standard medical procedures can be used to monitor the health and fitness of the subject. In addition, a parameter of metabolic activity (e.g., insulin levels) can be monitored.

In some embodiments, the cytochrome c-mediated apoptosis modulating agent is directed to a particular cell (e.g., by using a targeting vehicle or by using a cell-type specific regulatory sequence for a nucleic acid). For example, the agent can be targeting to an adipose, liver, pancreatic, brain, or skeletal muscle cell. In some examples, the targeted tissue participates in metabolic regulation.

Treatment of Unwanted Cell Proliferation in Subjects

Cell proliferation can be modulated to decrease, inhibit or prevent cell proliferation in disorders characterized by unwanted cell proliferation such as cancers. As described herein, deacetylating polypeptides interact with human cytochrome c protein to deacetylate cytochrome c. While not wishing to be bound by theory, a functional consequence of this deacetylation can be an increase of the cytochrome c's interaction with Apaf-1 and its apoptotic activity. Stress on a cell can result in release of cytochrome c from the mitochondria into the cytosol where in its non-acetylated form, it can interact with Apaf-1. Interaction of cytochrome c with Apaf-1 induces events (e.g., the activation of caspases) which can eventually result in apoptosis of the cell. Deacetylating cytochrome c, may enhance cytochrome c's ability to interact with Apaf-1 and induce cytochrome c-mediated apoptotic response. The formation of tumors is a multistep process requiring progressive accumulation of genetic alterations. Thus, cytochrome c release from the mitochondria due to stress, e.g., oncogenic stress, can play an important role in cancer by inducing apoptosis of damaged cells. A consequence of loss of pro apoptotic activity is the accumulation of the half-dozen or so mutations necessary for a cell to become carcinogenic. A second consequence may be uncontrolled cell growth, e.g., metastases, of the cell. In order to enhance or increase cytochrome c mediated apoptosis in these damaged cells, deacetylation, of cytochrome c is, preferably, reduced, inhibited or prevented.

Accordingly, in some aspect, the invention features methods of treating unwanted cell growth, e.g., in a subject having or at risk for cancer. The method includes administering a deacetylation agonist, e.g., a SIR agonist.

As used herein, the term "cancer" is meant to include all types of cancerous growths or oncogenic processes, metastatic tissues or malignantly transformed cells, tissues, or organs, irrespective of histopathologic type or stage of invasiveness. The cancer may be a malignant or non-malignant cancer. In some embodiments, the methods prevent or treat tumor proliferation and/or metastasis. Cancers or tumors include, but are not limited, to biliary tract cancer; brain cancer; breast cancer; cervical cancer; choriocarcinoma; colon cancer; endometrial cancer; esophageal cancer; gastric cancer; intraepithelial neoplasms; leukemias, lymphomas; liver cancer; lung cancer (e.g. small cell and non-small cell); melanoma; neuroblastomas; oral cancer; ovarian cancer; pancreatic cancer; prostate cancer; rectal cancer; sarcomas; skin cancer; testicular cancer; thyroid cancer; and renal cancer, as well as other carcinomas and sarcomas.

"Subject," as used herein, refers to human and non-human animals. The term "non-human animals" of the invention includes all vertebrates, e.g., mammals, such as non-human primates (particularly higher primates), sheep, dog, rodent (e.g., mouse or rat), guinea pig, goat, pig, cat, rabbits, cow, and non-mammals, such as chickens, amphibians, reptiles, etc. In a preferred embodiment, the subject is a human. In another embodiment, the subject is an experimental animal or animal suitable as a disease model.

In a preferred embodiment, the method includes administering a deacetylation agonist, e.g., a SIR agonist, in combination with one or more additional therapeutic agent or agents, e.g., a therapeutic agent or agents for treating unwanted cell proliferation.

The agonist can be used in combination with other therapies. For example, the combination therapy can include a deacetylation agonist, e.g., a SIR agonist, of the present invention co formulated with, and/or co administered with, one or more additional therapeutic agents, e.g., one or more anti-cancer agents, hormone treatment, vaccines, and/or other immunotherapies. Such combination therapies may advantageously utilize lower dosages of the administered therapeutic agents, thus avoiding possible toxicities or complications associated with the various monotherapies. In some embodiments, the administration of a deacetylation agonist enhances, e.g., sensitizes, cancer treatments with other anti-cancer agents. Thus, in some embodiments, the treatment is more effective because of combined administration. For example, the second treatment, e.g., the anti-cancer agent or other therapeutic agent, is more effective, e.g., an equivalent effect is seen with less of the second treatment, or the second treatment reduces symptoms to a greater extent, than would be seen if the second treatment were administered in the absence of the agonist. In some embodiments, delivery is such that the reduction in a symptom, or other parameter related to the disorder, is greater than what would be observed with the second treatment delivered in the absence of the agonist. The effect of the two treatments can be partially additive, wholly additive, or greater than additive. In some embodiments, the administration of an anti-cancer agent in combination with the agonist, may lower the dose of the anti-cancer agent or other therapeutic agents (e.g., hormone treatments), by at least 2, 3, 4, 5, 10, 15, 20, 30, 40, 50, 60% or more from the dose of the anti-cancer agent or other therapeutic agent administered in the absence of administration of the agonist.

Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concurrent delivery." In other embodiments, the delivery of one treatment ends before the delivery of the other treatment begins. The delivery can be such that an effect of the first treatment delivered is still detectable when the second is delivered.

In other embodiments, the agonists are administered in combination with other therapeutic treatment modalities, e.g., the existing modalities for treating cancer, including surgery and radiation.

In some embodiments, the agonist can be administered in combination with a high energy radiation emitters, for example, a radioisotope, such as $^{131}$I, a γ-emitter. Other suitable radioisotopes include α-emitters, such as $^{212}$Bi, $^{213}$Bi, and $^{211}$At, and β-emitters, such as $^{186}$Re and $^{90}$Y. Moreover, $Lu^{117}$ may also be used as an anti-cancer agent.

In some embodiments, the second therapeutic agent can be, for example, one or more of a chemotherapeutic agent and a cytotoxin. Examples of chemotherapeutic agents include taxol, cytochalasin B, gramicidin D, mitomycin, etoposide, tenoposide, vincristine, vinblastine, colchicin, busulfan, cisplatin, doxorubicin, daunorubicin, dihydroxy anthracin dione, mitoxantrone, mithramycin, chlorambucil, gemcitabine, actinomycin, procaine, tetracaine, lidocaine, propranolol, puromycin, maytansinoids and analogs or homologs thereof. Additional therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

The following examples are merely illustrative of particular aspects of the invention described herein.

EXAMPLES

The following examples demonstrate that cytochrome c is deacetylated by human SIRT2 and human SIRT3 using recombinant forms of the SIRT proteins as well as proteins derived from SIRT "pull downs" from cell extracts. The activity of these proteins was determined in vitro using either a $^{14}$C-nicotinamide release assay or a titrated acetate release assay.

Example 1

SIRT2 Deacetylation Activity on Cytochrome C

Recombinant GST-SIRT2 deacetylation activity was tested on chemically acetylated cytochrome c in the presence and absence of NAD. Deacetylation activity was determined in vitro using a titrated acetate release assay.

As shown in FIG. 1, recombinant GST-SIRT2 deacetylates cytochrome c in a NAD dependent manner.

Example 2

Recombinant SIRT3 Deacetylation Activity on Cytochrome C

Recombinant GST-SIRT3 deacetylation activity was tested on chemically acetylated cytochrome c in the presence and absence of NAD. The recombinant SIRT3 was a fragment of human SIRT3 lacking the first 100 amino acids of the N-terminus of full length human SIRT3. Deacetylation activity was determined in vitro using a titrated acetate release assay.

Figure 2:
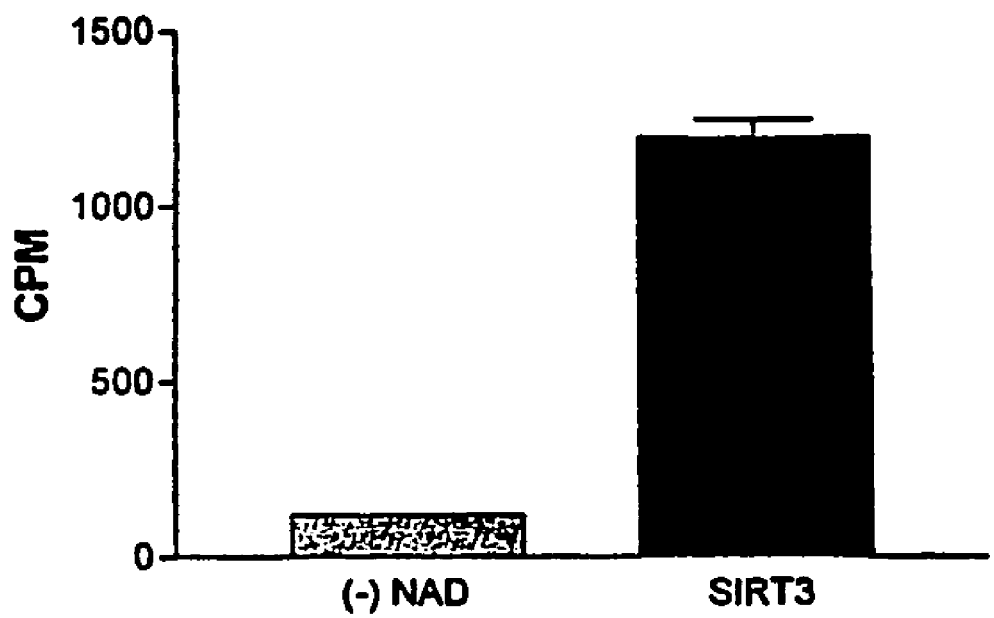
FIG. 2 is a graph showing recombinant GST-SIRT3 deacetylation of acetylated cytochrome c in the presence or absence of NAD.

As shown in FIG. 2, recombinant GST-SIRT3 deacetylates cytochrome c in a NAD dependent manner.

Example 3

Cell Derived SIRT3 Deacetylation Activity on Cytochrome C

Cell derived GST-SIRT3 deacetylation activity was tested on chemically acetylated cytochrome c. The SIRT3 was derived from "pull down" 293T extracts.

Deacetylation activity was determined in vitro using a $^{14}$C-nicotinamide release assay. Deacetylation was determined for GFP (control) with chemically acetylated cytochrome c, SIRT3-GFP with chemically acetylated cytochrome c, and SIRT3-GFP with histone 4.

Figure 3:
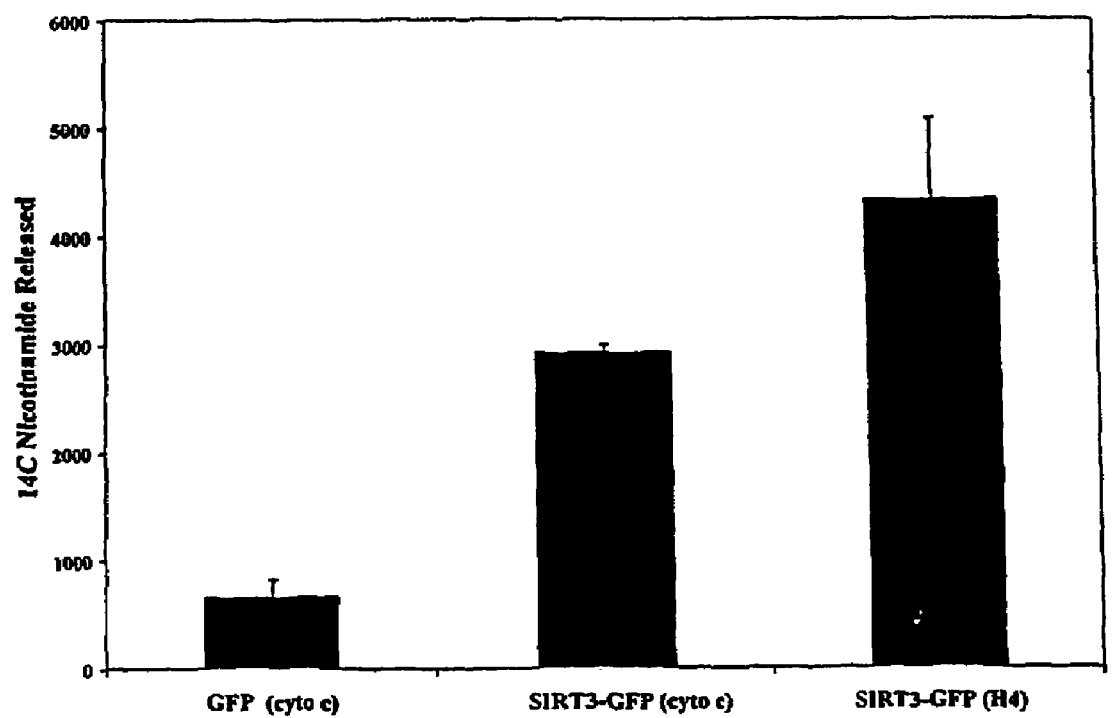
FIG. 3 is a graph showing deacetylation of chemically acetylated cytochrome c by SIRT3 enzyme derived from pull downs of 293T cell extracts in nicotinamide release assays of SIRT3-GFP or GFP (control) proteins. The substrate is indicated in parentheses (cytochrome c or histone H4).

As shown in FIG. 3, cell derived SIRT3 deacetylates cytochrome c.

Example 4

Cell Derived SIRT1-7 Deacetylation Activity on Cytochrome C

Deacetylation activity was tested for cell derived SIRT1, Sirt2, SIRT3, SIRT5, SIRT6 and SIRT7 on chemically acetylated cytochrome c. The SIRT enzymes were derived from "pull down" 293T extracts expressing the respective SIRT family member.

Deacetylation activity was determined in vitro using a $^{14}$C-nicotinamide release assay. Deacetylation was determined for a control reaction mixture with cytochrome c, SIRT1 with cytochrome c, SIRT2, with cytochrome c, SIRT3 with cytochrome c, SIRT5 with cytochrome c, SIRT6 with cytochrome c and SIRT7 with cytochrome c.

Figure 4:
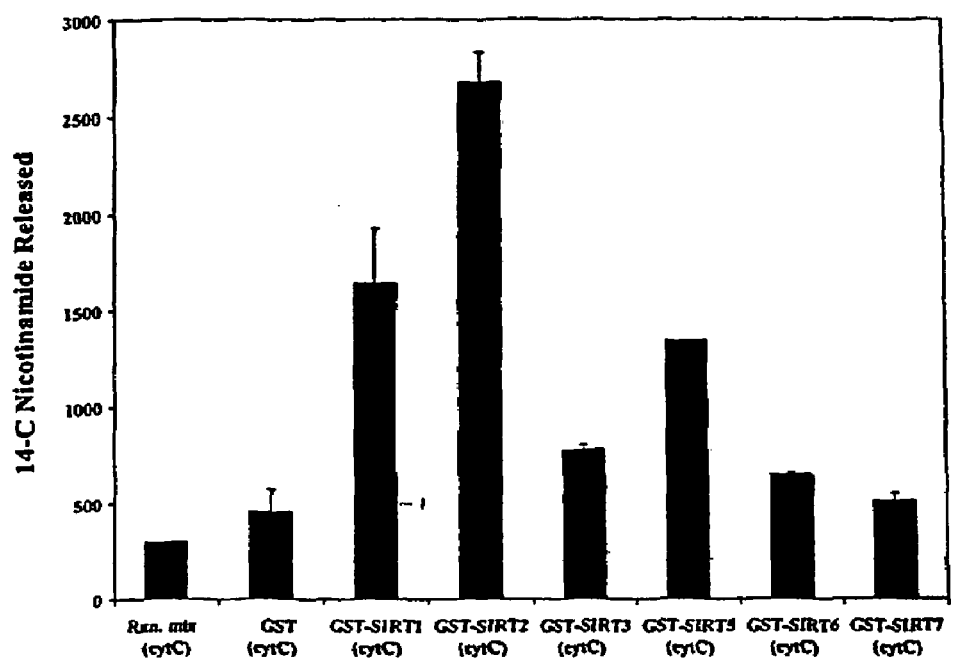
FIG. 4 is a graph depicting deacetylation of chemically acetylated cytochrome c by SIRT1-7 enzymes derived from pull downs of 293T cell extracts in nicotinamide release assays. The substrate cytochrome c is indicated in parentheses.

The results are shown in FIG. 4.

A number of embodiments of the invention have been described. Nevertheless, it will be understood that various modifications may be made without departing from the spirit and scope of the invention. Accordingly, other embodiments are within the scope of the following claims.

What is claimed:

1. A method of evaluating a compound, the method comprising
    contacting a Silent Information Regulator (SIR) polypeptide having deacetylase activity with the compound in vitro, in the presence of a cytochrome c polypeptide, wherein the amino acid sequence of the SIR polypeptide comprises an amino acid sequence that is at least 95% identical to the amino acid sequence of SEQ ID NO: 1, and
    evaluating if the compound modulates interaction between the SIR polypeptide and the cytochrome c polypeptide.

2. The method of claim 1, wherein the cytochrome c polypeptide is acetylated at at least one lysine.

3. The method of claim 1, wherein the cytochrome c polypeptide is human cytochrome c polypeptide.

4. The method of claim 1, wherein the SIR polypeptide comprises the amino acid sequence of SEQ ID NO: 1.

5. A method comprising:
    contacting a cultured cell which expresses a SIR polypeptide having deacetylase activity and a cytochrome c polypeptide with a test compound, wherein the amino acid sequence of the SIR polypeptide comprises an amino acid sequence that is at least 95% identical to the amino acid sequence of SEQ ID NO: 1, and
    determining if the test compound modulates acetylation of the cytochrome c polypeptide.

6. The method of claim 5 further comprising evaluating apoptosis or an indication of apoptosis in the cell.

7. A method of evaluating a test compound, the method comprising:
    contacting a SIR polypeptide having deacetylase activity with the test compound, in the presence of a cytochrome c polypeptide, in vitro, wherein the amino acid sequence of the SIR polypeptide comprises an amino acid sequence that is at least 95% identical to the amino acid sequence of SEQ ID NO: 1,
    evaluating if the test compound modulates interaction between the SIR polypeptide and the cytochrome c polypeptide;
    contacting a cultured cell which expresses the SIR polypeptide and a cytochrome c polypeptide with the test compound, and
    determining if the test compound modulates acetylation of the cytochrome c polypeptide in the cell.

8. The method of claim 7, wherein the SIR polypeptide comprises the amino acid sequence of SEQ ID NO: 1.

9. The method of claim 1, wherein NAD or an NAD analog is present during the contacting step.

10. The method of claim 5, wherein NAD or an NAD analog is present during the contacting step.

11. The method of claim 7, wherein NAD or an NAD analog is present during the contacting step.

12. The method of claim 5, wherein the SIR polypeptide comprises the amino acid sequence of SEQ ID NO: 1.

13. The method of claim 5, wherein the cytochrome c polypeptide is acetylated at at least one lysine.

14. The method of claim 5, wherein the cytochrome c polypeptide is human cytochrome c polypeptide.

15. The method of claim 7, wherein the cytochrome c polypeptide is acetylated at at least one lysine.

16. The method of claim 7, wherein the cytochrome c polypeptide is human cytochrome c polypeptide.

17. The method of claim 1, wherein the cytochrome c polypeptide is acetylated.

18. The method of claim 5, wherein the cytochrome c polypeptide is acetylated.

19. The method of claim 7, wherein the cytochrome c polypeptide is acetylated.

20. A method of evaluating a compound, the method comprising
    contacting a cultured cell which expresses a SIR polypeptide having deacetylase activity with the compound, in the presence of a cytochrome c polypeptide, wherein the amino acid sequence of the SIR polypeptide comprises an amino acid sequence that is at least 95% identical to the amino acid sequence of SEQ ID NO: 1, and
    evaluating if the compound modulates interaction between the SIR polypeptide and the cytochrome c polypeptide.

21. The method of claim 20, wherein the cytochrome c polypeptide is acetylated at at least one lysine.

22. The method of claim 20, wherein the cytochrome c polypeptide is human cytochrome c polypeptide.

23. The method of claim 20, wherein the SIR polypeptide comprises the amino acid sequence of SEQ ID NO: 1.

24. The method of claim 20, wherein NAD or an NAD analog is present during the contacting step.

25. The method of claim 20, wherein the cytochrome c polypeptide is acetylated.

26. A method comprising:
    contacting a SIR polypeptide having deacetylase activity and a cytochrome c polypeptide with a test compound in vitro, wherein the amino acid sequence of the SIR polypeptide comprises an amino acid sequence that is at least 95% identical to the amino acid sequence of SEQ ID NO: 1, and
    determining if the test compound modulates acetylation of the cytochrome c polypeptide.

27. The method of claim 26, wherein NAD or an NAD analog is present during the contacting step.

28. The method of claim 26, wherein the SIR polypeptide comprises the amino acid sequence SEQ ID NO: 1.

29. The method of claim 26, wherein the cytochrome c polypeptide is acetylated at at least one lysine.

30. The method of claim 26, wherein the cytochrome c polypeptide is human cytochrome c polypeptide.

31. The method of claim 26, wherein the cytochrome c polypeptide is acetylated.

* * * * *